United States Patent [19]

Boyd et al.

[11] Patent Number: 5,783,598
[45] Date of Patent: *Jul. 21, 1998

[54] ANTIRETROVIRAL NAPHTHOQUINONE COMPOUNDS COMPOSITIONS AND USES THEREOF

[75] Inventors: Michael R. Boyd. Ijamsville; John H. Cardellina, II. Walkersville; Kirk R. Gustafson. Mt. Airy. all of Md.; Laurent A. Decosterd. Nyon. Switzerland; Ian Parson. Ithaca. N.Y.; Lewis Pannell. Silver Spring. Md.; James B. McMahon. Frederick. Md.; Gordon M. Cragg. Bethesda. Md.

[73] Assignee: The United States of America as represented by the Secretary of the Department of Health and Human Sevices, Washington. D.C.

[*] Notice: The term of this patent shall not extend beyond the expiration date of Pat. No. 5.672.607.

[21] Appl. No.: 613,162

[22] Filed: Mar. 8, 1996

Related U.S. Application Data

[63] Continuation of Ser. No. 11,183, Jan. 29, 1993, Pat. No. 5,672,607.
[51] Int. Cl.$^6$ ......................... A61K 31/35; C07D 407/14
[52] U.S. Cl. .............................................. 514/454; 549/389
[58] Field of Search ........................... 514/454; 549/388, 549/389

[56] References Cited

PUBLICATIONS

Stein et al.. Immune–Based Therapeutics. Clinical Infectious Diseases. 17:749–71. 1993.
Fahey et al.. Status of immune–based therapies, Clin. exp. Immunol., 88, 1–5, 1992.
Fox. No Winners Against AIDS. Bio/Technology. 12: 128. 1994.
Boyd. in *AIDS Etiology, Diagnosis, Treatment and Prevention* (DeVita et al., eds.), 305–319 (Philadelphia: Lippincott. 1988).
Cameron et al.. *Aust. J. Chem.*, *31*, 1323–1333 (1978).
Cannon et al.. *Tetrahedron Lett.*, *32*, 2795–2798 (1975).
Decosterd et al.. *J. Am. Chem. Soc.*, *115* (15), 6673–6679 (1993).
Durley et al.. *J. Chem. Soc. Perkin 1*, 153–169 (1975).
Gulakowski et al.. *J. Virol. Methods*, *33*, 87–100 (1991).
Gustafson et al.. *J. Med. Chem.*, *35*, 1978–1986 (1992).
Jeffreys et al.. *Tetrahedron Lett.*, *24*, 1085–1088 (1983).
Jurd. *Aust. J. Chem.*, *33*, 1603–1610 (1980).
McCaffrey et al.. *In Vitro Cell Develop. Biol.*, *24*, 247–252 (1988).
Rink et al.. *J. Cell. Biol.*, *95*, 189–196 (1982).
Shih et al.. *PNAS*, *88*, 9878–9882 (1991).
Singh et al.. *The Journal of Antibiotics*, *38*, 706–712 (1985).
Waterman et al.. *J. Chem. Res.* (M). 101–144 (1985).
Weislow et al.. *J. Natl. Cancer Inst.*, *81* (8), 577–586 (1989).
White et al.. *Antiviral Research*, *16*, 257–266 (1991).

*Primary Examiner*—Joseph McKane
*Attorney, Agent, or Firm*—Leydig. Voit & Mayer. Ltd.

[57] ABSTRACT

The present invention provides novel antiviral naphthoquinone compounds, which may be isolated from plants of the genus Conospermum or synthesized chemically, in accordance with the present inventive methods. The antiviral naphthoquionone compounds, derivatives thereof, and prodrugs thereof, may be used alone or in combination with other antiviral agents in compositions, such as pharmaceutical compositions, to inhibit the growth or replication of a virus, such as a retrovirus, in particular a human immunodeficiency virus, specifically HIV-1 or HIV-2, in the treatment or prevention of viral infection.

21 Claims, 12 Drawing Sheets

COMPOUND 2  ($R_1$=OH, $R_2$=H)
COMPOUND 6  ($R_1$=p-OCOC$_6$H$_4$Br, $R_2$=H)
COMPOUND 7  ($R_1$=$R_2$=SC$_6$H$_5$)
COMPOUND 8  ($R_1$=$R_2$=H)

COMPOUND 1

COMPOUND 4

COMPOUND 3

COMPOUND 9

COMPOUND 5

COMPOUND 10

ANTIRETROVIRAL NAPHTHOQUINONE COMPOUNDS COMPOSITIONS AND USES THEREOF

This is a continuation of application Ser. No. 08/011,183, filed on Jan. 29, 1993, now U.S. Pat. No. 5,672,607.

TECHNICAL FIELD OF THE INVENTION

This invention relates to antiviral compounds, in particular antiviral compounds obtained from plants of the genus Conospermum, specifically compounds referred to as naphthoquinones. This invention also relates to methods of obtaining antiviral compounds, specifically naphthoquinones and derivatives thereof, in substantially pure form, from Conospermum plants. This invention also relates to synthetic naphthoquinones and derivatives thereof and to methods of chemically synthesizing both. This invention further relates to compositions comprising antiviral naphthoquinones, derivatives thereof, or prodrugs thereof, and methods of using the compositions in clinical applications, such as antiviral therapy and the prevention of viral infection.

BACKGROUND OF THE INVENTION

Acquired immune deficiency syndrome (AIDS) is a fatal disease, reported cases of which have increased dramatically within the past several years. Estimates of reported cases in the very near future also continue to rise dramatically. Consequently, there is a great need to develop drugs and vaccines to combat AIDS.

The AIDS virus was first identified in 1983. It has been known by several names and acronyms. It is the third known T-lymphocyte virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (HIV). Two distinct families of HIV have been described to date, namely HIV-1 and HIV-2. The acronym HIV will be used herein to refer to HIV viruses generically.

Specifically, HIV is known to exert a profound cytopathic effect on the CD4+ helper/inducer T-cells, thereby severely compromising the immune system. HIV infection also results in neurological deterioration and, ultimately, in the death of the infected individual.

The field of viral chemotherapeutics has developed in response to the need for agents effective against retroviruses, in particular HIV. There are many ways in which an agent can exhibit anti-retroviral activity. For example, HIV requires at least four viral proteins for replication: reverse transcriptase (RT), protease (PR), transactivator protein (TAT), and regulator of virion-protein expression (REV). Accordingly, viral replication could theoretically be inhibited through inhibition of any one or all of the proteins involved in viral replication.

Anti-retroviral agents, such as AZT and ddC, are known to inhibit RT. There also exist antiviral agents that inhibit TAT.

Nucleoside derivatives, such as AZT, are the only clinically active agents that are currently available for antiviral therapy. Although very useful, the utility of AZT and related compounds is limited by toxicity and insufficient therapeutic indices for fully adequate therapy.

Synthetic peptides also are being developed for potential use as inhibitors of the retroviral PR in the treatment of AIDS. Although these inhibitors are effective in preventing the retroviral PR from functioning, the inhibitors suffer from some distinct disadvantages. First, since the active site of the PR is hindered, i.e., has reduced accessibility as compared to the remainder of the PR, the ability of the inhibitors to access and bind in the active site of the PR is impaired. Secondly, the peptide inhibitors that bind to the active site of the PR are generally poorly soluble in water, causing distinct problems in drug delivery.

Therefore, new classes of antiviral agents to be used alone or in combination with AZT and/or other agents are urgently needed for effective antiviral therapy against HIV. New agents which may be used to prevent HIV infection are also important.

It is an object of the present invention to provide novel antiviral compounds, in particular antiviral compounds obtained from plants of the genus Conospermum, specifically compounds referred to as naphthoquinones and derivatives thereof, and naphthoquinones and derivatives thereof synthesized chemically. It is another object of the present invention to provide a method of obtaining novel antiviral compounds, specifically naphthoquinones and derivatives thereof, by isolation from plants of the genus Conospermum or by chemical synthesis.

It is still another object of the present invention to provide a novel composition, in particular a pharmaceutical composition, which inhibits the growth or replication of a virus, such as a retrovirus, in particular a human immunodeficiency virus, specifically HIV-1 or HIV-2. Yet another object of the present invention is to provide a novel method of treating an animal, in particular a human, infected with a virus, such as a retrovirus, in particular a human immunodeficiency virus, specifically HIV-1 or HIV-2.

It is an additional object of the present invention to provide a novel composition, in particular a pharmaceutical composition, which prevents infection of an animal, in particular a human, with a virus, such as a retrovirus, in particular a human immunodeficiency virus, specifically HIV-1 or HIV-2. A related object of the present invention is to provide a novel method of treating an animal, in particular a human, to prevent infection with a virus, such as a retrovirus, in particular a human immunodeficiency virus, specifically HIV-1 or HIV-2.

These and other objects of the present invention, as well as additional inventive features, will become apparent from the description herein.

BRIEF SUMMARY OF THE INVENTION

The present invention provides novel antiviral, compounds, in particular antiviral compounds, in substantially pure form, isolated from plants of the genus Conospermum, specifically compounds referred to as naphthoquinones and derivatives thereof, and to chemically synthesized naphthoquinones and derivatives thereof. The present invention also provides for a method of obtaining, in substantially pure form, novel antiviral compounds, specifically naphthoquinones and derivatives thereof, from Conospermum plants or by chemical synthesis. The compounds so obtained may be used in a composition, such as a pharmaceutical composition, which may additionally comprise one or more other antiviral agents. Such compounds have been found to inhibit the growth or replication of a virus, in particular a retrovirus, specifically a human immunodeficiency virus, such as HIV-1 or HIV-2. The compounds and related compositions, therefore, are expected to have utility in the therapeutic treatment of animals, such as a humans, infected with a virus, particularly a retrovirus, specifically a human immunodeficiency virus, such as HIV-1 or HIV-2, or in the prophylactic treatment of an animal, such as a human, to prevent viral infection.

DETAILED DESCRIPTION OF THE PREFERRED EMBODIMENTS

Figure 1B:
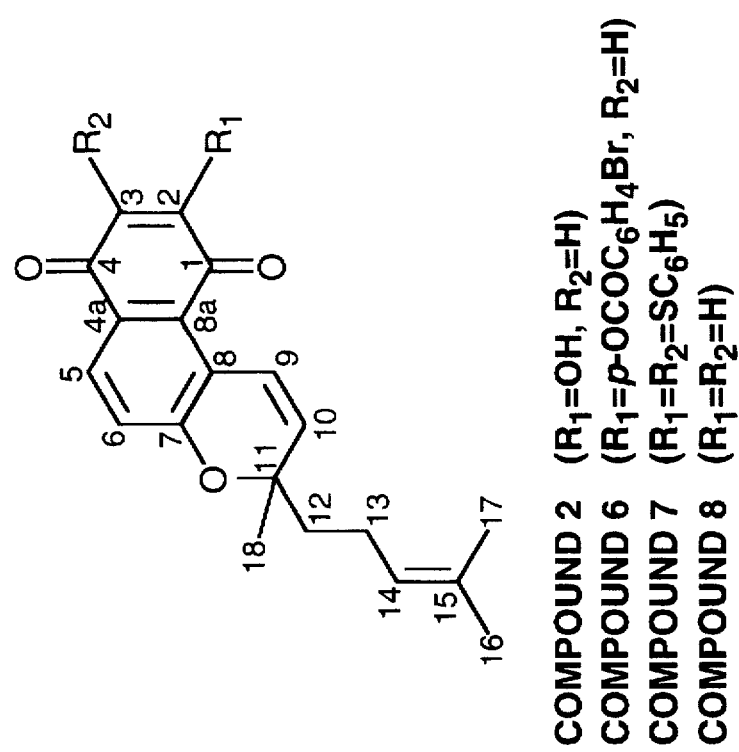
FIGS. 1A–1G illustrates the structure of conocurvone (1) (FIG. 1A) and related naphthoquinone compounds (2–8) (FIG. 1B (compounds 2 and 6–8), FIG. 1C (compound 3), FIG. 1D (compound 4), and FIG. 1E (compound 5)) isolated, in substantially pure form, from Conospermum sp. (Spjut 7139) or prepared as synthetic derivatives of compounds isolated from Conospermum plants and related synthetic naphthoquinone compounds (9 and 10) (FIGS. 1F and 1G, respectively).

The present invention provides novel antiviral compounds, specifically naphthoquinones and derivatives thereof (hereinafter collectively referred to as "naphthoquinones"), in substantially pure form and having, for example, the structures:

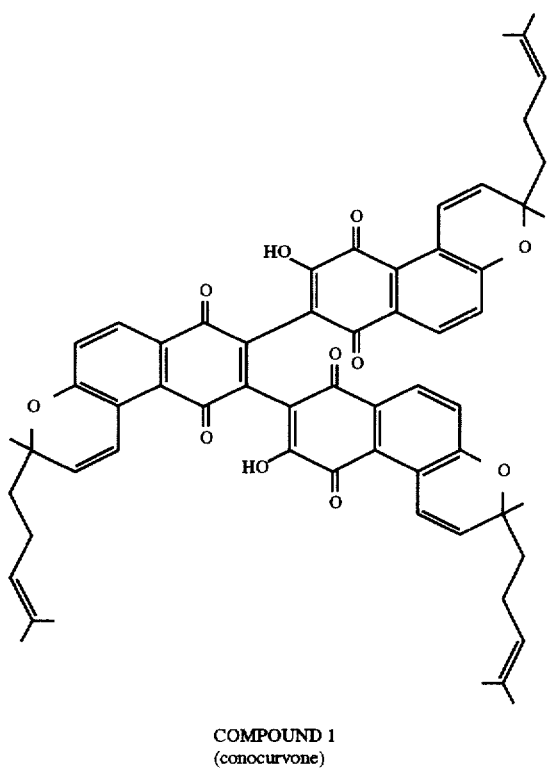

COMPOUND 1
(conocurvone)

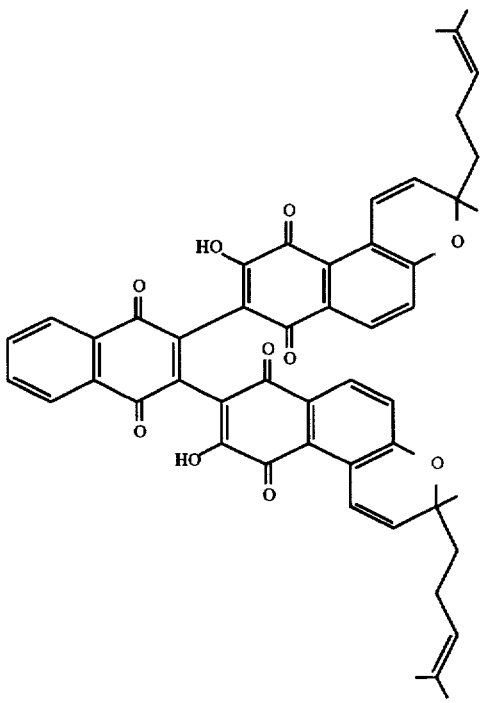

COMPOUND 4

-continued
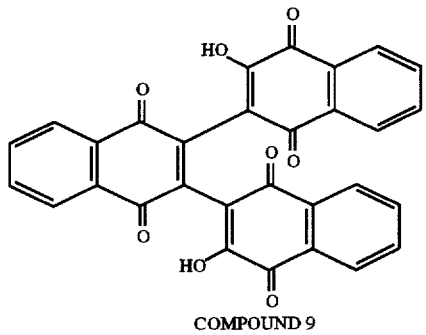
COMPOUND 9
-continued
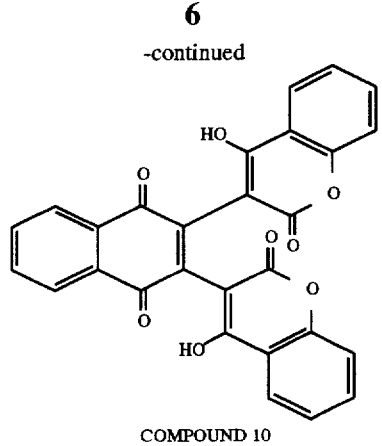
COMPOUND 10
The antiviral naphthoquinones and antiviral derivatives thereof may be described further as having the generic structures below, wherein $R_1$–$R_{12}$ each are the same or different, and each may be H, a $C_1$–$C_{10}$ straight-chain or branched chain saturated or unsaturated alkyl, an aryl, $OCH_3$, or OH:
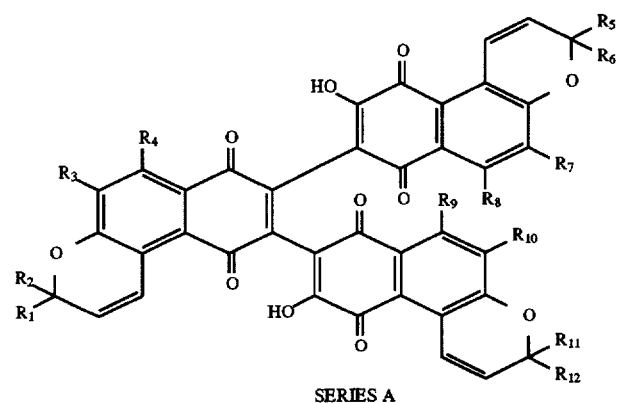
SERIES A
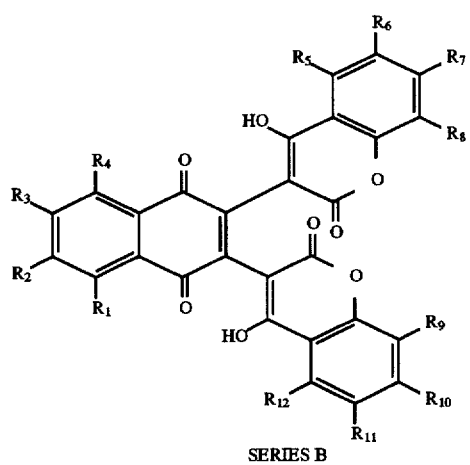
SERIES B
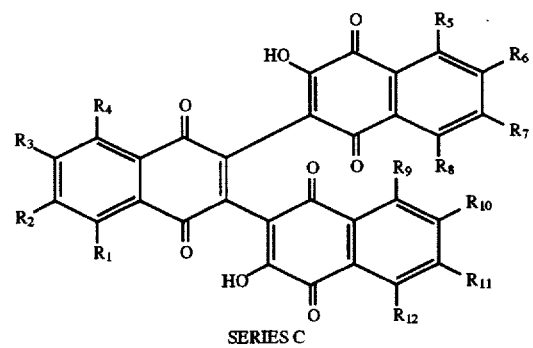
SERIES C -continued

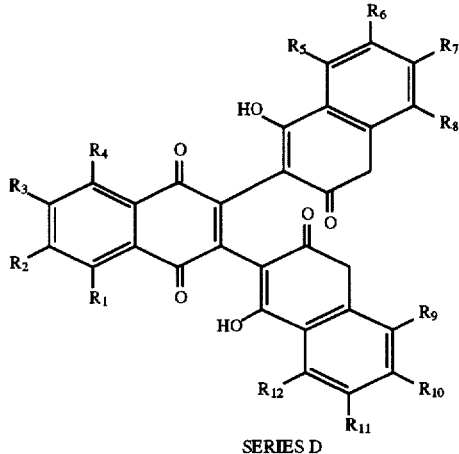

SERIES D

The present invention also provides a method of isolating and purifying antiviral naphthoquinones and derivatives thereof from plants of the genus Conospermum, which comprises the steps of:

(a) extracting dried plant material with organic solvents to obtain a crude extract;

(b) performing an antiviral, such as an anti-HIV, bioassay-directed isolation and purification of active antiviral naphthoquinones and derivatives thereof by:

(i) solvent-solvent partitioning of the crude extract to obtain an antiviral, e.g., anti-HIV, active fraction;

(ii) subjecting the antiviral, e.g., anti-HIV, active fraction to centrifugal countercurrent chromatography to obtain an enriched antiviral, e.g., anti-HIV, active fraction;

(iii) subjecting the enriched antiviral, e.g., anti-HIV, active fraction to low pressure column chromatography and/or gel permeation chromatography to obtain crude, semipure antiviral, e.g., anti-HIV, active compound; and (iv) subjecting the semipure antiviral, e.g., anti-HIV active compound to high pressure liquid chromatography (HPLC) to obtain an antiviral, e.g., anti-HIV, active naphthoquinone or derivative thereof in substantially pure form.

The present invention further provides a method for synthesizing antiviral naphthoquinones and derivatives thereof, wherein precursors, which have been isolated from plants of the genus Conospermum, synthesized chemically, or obtained commercially, are used. The method comprises the steps of:

(a) acid- or base-catalyzed coupling an appropriately substituted or unsubstituted 2,3-deoxy-1,4-naphthoquinone compound with two other subunits, each of which may be the same or different and each of which may be an appropriately substituted or unsubstituted 3-hydroxy-1,4-naphthoquinone or 2-hydroxy-1,4-naphthoquinone compound, to yield a corresponding antiviral trimeric naphthoquinone compound; and (b) purifying, to substantially pure form, the desired antiviral trimeric naphthoquinone compound. If the necessary 2,3-deoxy-1,4-naphthoquinone is unavailable, it may be prepared from the corresponding 3-hydroxy- or 2-hydroxy-1,4-naphthoquinone compound by removal of the 3-hydroxyl or 2-hydroxyl group by the steps of:

(i) preparing the corresponding 3- or 2-p-bromobenzoate derivative;

(ii) treating the corresponding 3- or 2-p-bromobenzoate derivative with thiophenol to form the corresponding 2,3 bisthiophenol adduct; and (iii) Raney nickel reducing the corresponding 2,3 bisthiophenol adduct to yield the desired corresponding 2,3-deoxy-1,4-naphthoquinone compound.

The desired antiviral trimeric naphthoquinone compound may be purified by any suitable means, for example, using, as necessary, solvent-solvent partitioning, gel permeation chromatography, low pressure column chromatography, centrifugal countercurrent chromatography, or HPLC, with, as appropriate, an antiviral, e.g., anti-HIV, bioassay of fractions and compounds.

The antiviral naphthoquinone compounds, obtained in accordance with the present inventive method, may be used alone or in combination with other antiviral agents in compositions, such as pharmaceutical compositions, to inhibit the growth or replication of a virus, such as a retrovirus, in particular a human immunodeficiency virus, specifically HIV-1 or HIV-2. It is expected that such compositions will have utility in the therapeutic treatment of an animal, in particular a human, infected with one or more of the above-cited viruses and in the prophylactic treatment of an animal, in particular a human, who is at risk for infection with one or more of the same viruses.

Prior to the discovery on which this invention is based, the antiviral naphthoquinone compounds had not been isolated or described. Methods for isolating such antiviral compounds had not been determined. Accordingly, the antiviral activity of these compounds was not previously known, and the potential use of these compounds in compositions, such as pharmaceutical compositions, in the therapeutic and prophylactic treatment of viral infections in animals, in particular humans, had not been recognized.

An initial observation, which led to the present invention, was the antiviral activity of an extract (coded N4953) from a plant named Conospermum sp. (Spjut 7139) in an anti-HIV screen. The screen is one that was conceived in 1986 (M. R. Boyd of the National Institutes of Health, DTP, NCI) and has been developed and operated at the U.S. National Cancer Institute since 1988 (see Boyd, M. R., in *AIDS, Etiology, Diagnosis, Treatment and Prevention* (DeVita V. T., Jr., Hellman S., Rosenberg S. A., eds.), pp. 305–319 (Philadelphia: Lippincott, 1988)).

The genus Conospermum is one of approximately 62 genera in the plant family Proteaceae. All of the known species in the genus Conospermum are endemic to the Australian continent. The dried Conospermum sp. (Spjut 7139) plants, from which the extracts leading to the present invention were obtained, were collected in 1981 by R. Spjut (under an NCI/USDA interagency agreement) in the Gairdner mountain range of western Australia, midway between Geraldton and Perth. Voucher specimens of the Conospermum sp. (Spjut 7139) have been placed on deposit with the U.S. National Arboretum and the Smithsonian Institute.

Previous studies of Conospermum species had identified a series of simple monomeric naphthoquinone compounds (Cannon, J. R., et al., Tetrahedron Lett., 2795–2798, 1975). However, antiviral activity had not been associated with any compounds from this genus.

The Conospermum extracts leading to the present invention were among many thousands of different plant extracts initially selected randomly and tested blindly in the anti-HIV screen described above. A specific bioassay-guided strategy was used to isolate and purify the individual bioactive compounds from the extracts of the plant Conospermum sp. (Spjut 7139) found active in the screen. In this strategy, the initial selection of the Conospermum extract for fractionation, as well as the decisions concerning the overall chemical isolation method to be applied, and the nature of the individual steps therein, were determined by interpretation of biological testing data.

Figure 1A:
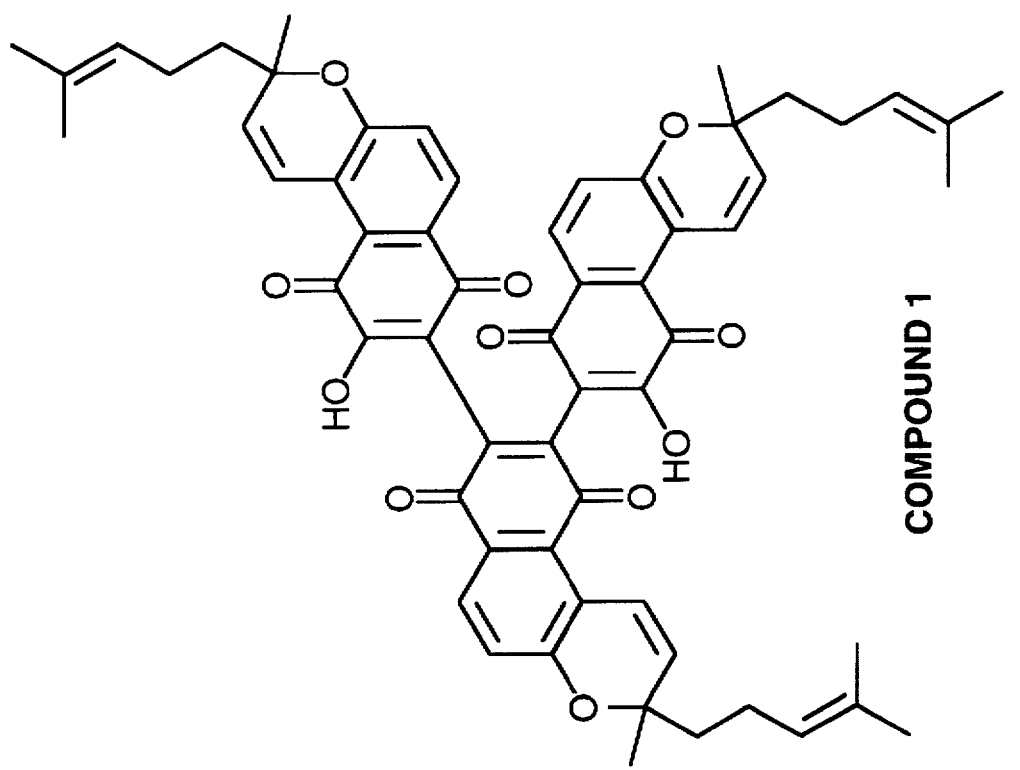
Figure 1D:
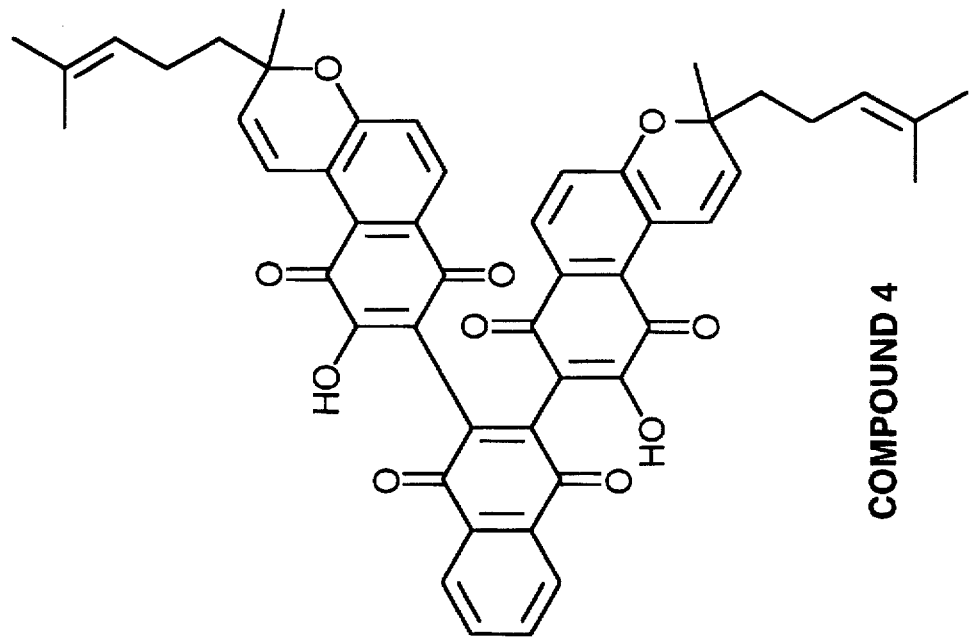
Figure 1C:
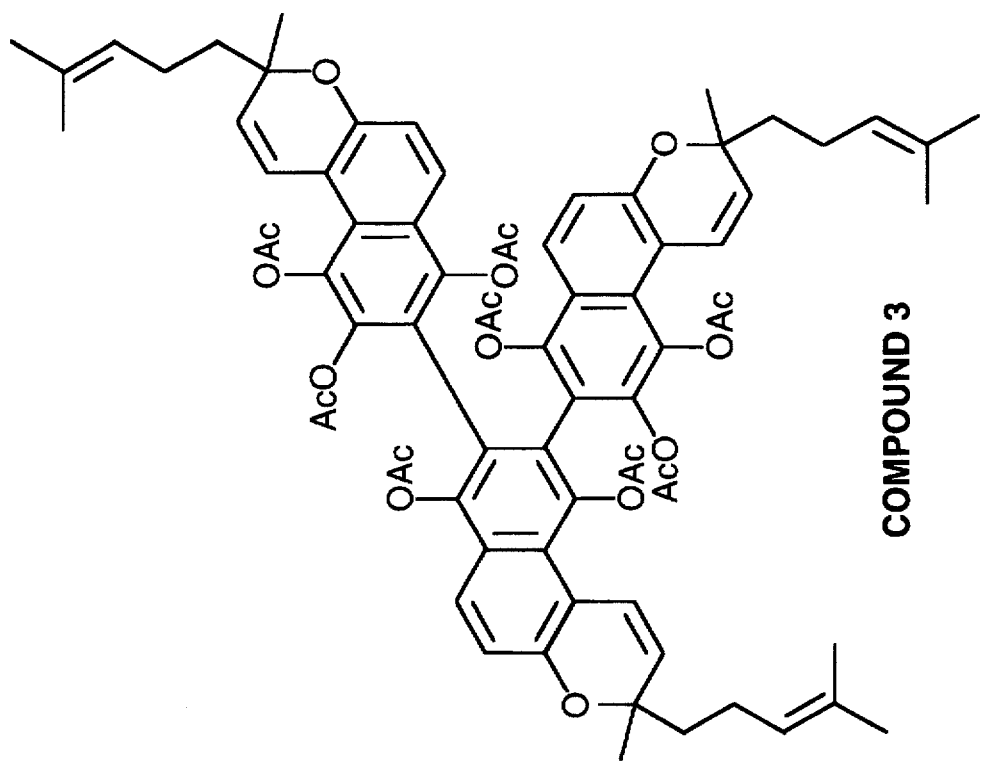
Figure 1F:
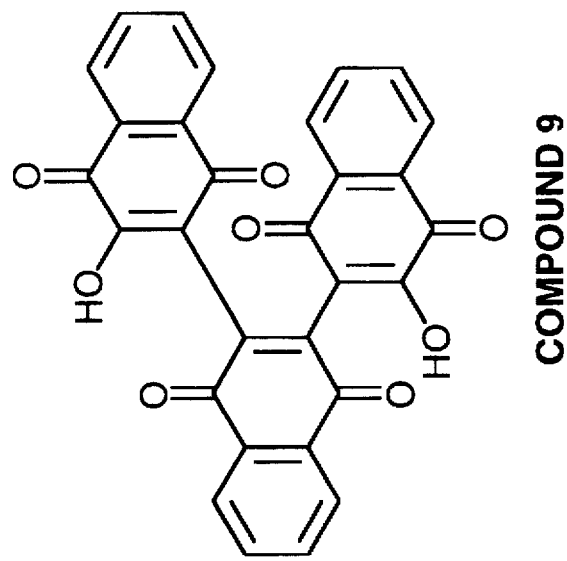
Figure 1E:
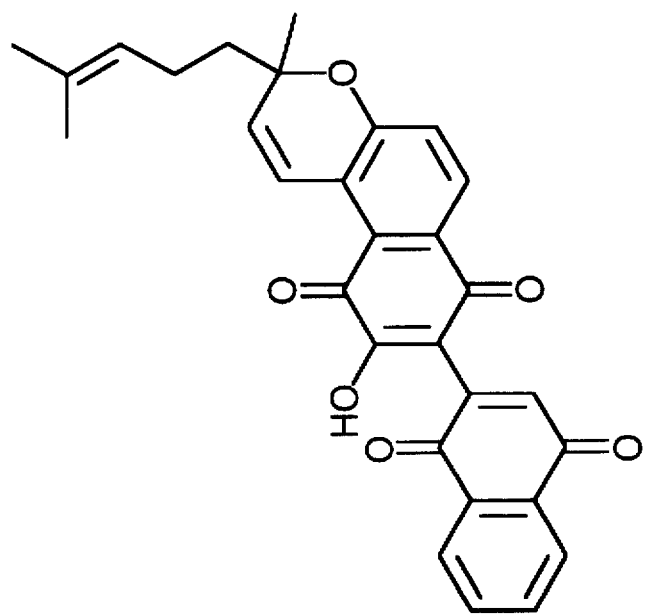
Figure 1G:
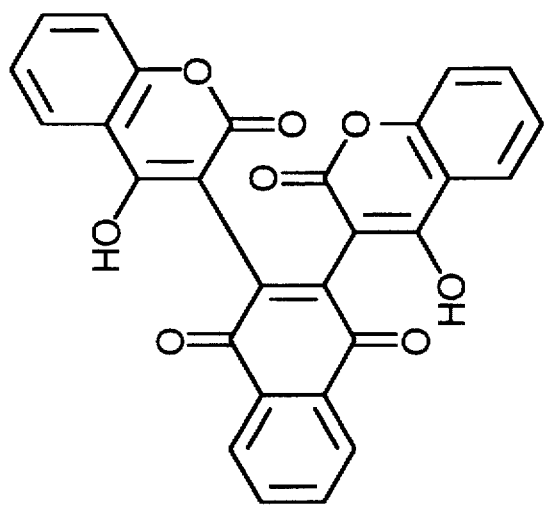

The anti-HIV screening assay (Weislow, O. S. et al., J. Natl. Cancer Inst., 81(8): 577–586, 1989) used to guide the isolation and purification process measured the degree of protection of human T-lymphoblastoid cells from the cytopathic effects of HIV. Fractions of the extracts were prepared using a variety of chemical means arid were tested blindly in the primary screen. Active fractions were separated further, and the resulting subfractions were tested blindly in the screen. This process was repeated as many times as necessary in order to obtain the active compound(s), i.e., antiviral fraction(s) representing pure compound(s), which then could be subjected to detailed chemical analysis and structural elucidation. In this manner, conocurvone (compound 1 of FIG. 1A), the first representative of the new antiviral class of compounds described herein, was discovered. A previously reported naphthoquinone compound called teretifolione B (J. R. Cannon, et al., Tetrahedron Lett., 2795–2798, 1975) (compound 2 of FIG. 1B) was re-isolated from a Conospermum sp., but it was devoid of anti-HIV activity.

Although Conospermum sp. (Spjut 7139) was used as the plant source of conocurvone in the present invention, it will be appreciated that such compounds also may be obtained by isolation from other plant species of the same genus, such as, for example, Conospermum incurvum, C. stoechadis, and C. triplinervium. A variety of methods can be used to isolate conocurvone from plants. These methods include extraction, solvent-solvent partitioning, high speed countercurrent chromatography, low pressure column chromatography, and HPLC with a variety of bonded phases. The isolation of conocurvone can be monitored by a combination of ultraviolet (UV), thin layer chromatography (TLC), and anti-HIV bioassay. A typical isolation procedure is set forth below.

Approximately 1 kilogram of air-dried plant material, consisting of leaves, twigs, seeds, fruit, bark or roots, is first ground to a fine powder and extracted with 1:1 MeOH—$CH_2Cl_2$ and then washed with 100% MeOH. After evaporation of solvent, these organic extracts typically amount to a total of about 2–20% of the mass of the starting plant material. The initial crude extract is dissolved in 9:1 MeOH-$H_2O$ and extracted with hexane.

The anti-HIV activity is concentrated in the 9:1 MeOH—$H_2O$ fraction, which is then partitioned between either $CH_2Cl_2$ or $CCl_4$ and 7:3 MeOH—$H_2O$. The $CH_2Cl_2$- or $CCl_4$-soluble material can be preliminarily fractionated by centrifugal countercurrent chromatography with hexane/EtOH/EtOAc/$H_2O$ (5:4:2:1, ascending mode). Anti-HIV fractions from the countercurrent chromatograph are pooled.

The anti-HIV active fractions may be further separated by low pressure column chromatography on diol bonded phase packing eluted with increasingly polar mixtures of hexane/EtOAc and/or by gel permeation on Sephadex LH-20 eluted with 2:5:1 hexane/$CH_2Cl_2$/MeOH or 1:1 $CH_2Cl_2$/MeOH. Final purification of the active material is achieved by HPLC, using a phenyl bonded phase column eluted with $CH_3CN$/$H_2O$ (17:3, 0.1% HOAC by vol) to give pure conocurvone. Using this procedure, the pure active compound generally can be obtained in a net overall yield of about 0.05–0.5% from the original amount of crude extract. The isolation of conocurvone is described in greater detail in Example 1.

Antiviral naphthoquinone compounds of the present invention also may be obtained by chemical synthesis. Precursor or subunit compounds required for synthesis of the antiviral naphthoquinone compounds of the present invention may be readily obtained by isolation from natural sources (specifically plants of the genus Conospermum), chemical synthesis, chemical semisynthesis, or from commercial sources. The antiviral trimeric naphthoquinone compounds may be made by the acid- or base-catalyzed coupling of an appropriately substituted or unsubstituted 2,3-deoxy-1,4-naphthoquinone compound with two appropriately substituted or unsubstituted 2-hydroxy-1,4-naphthoquinone or 3-hydroxy-1,4-naphthoquinone compound subunits. The corresponding anti-HIV active trimeric naphthoquinone products are isolated and purified from the reaction mixtures by techniques, such as those described above, for obtaining such compounds, in substantially pure form, from extracts of plants. A typical synthesis procedure is set forth below.

Reaction, in a solution with glacial acetic acid or pyridine, of an appropriately substituted or unsubstituted 2,3-deoxy-1,4-naphthoquinone compound with two equivalents of an appropriately substituted or unsubstituted 3-hydroxy-1,4-naphthoquinone compound and/or 2-hydroxy-1,4-naphthoquinone compound, followed by anti-HIV bioassay-guided isolation and purification, will yield antiviral trimeric naphthoquinone compounds. If otherwise unavailable, the necessary 2,3-deoxy-1,4-naphthoquinone compound for the above reaction may be prepared from the corresponding 3-hydroxy- or 2-hydroxy-1,4-naphthoquinone compound. For example, conocurvone itself (1) can be prepared from teretifolione B (2). The central dehydroxymonomeric subunit of compound 1 is produced by removal of the C2 hydroxyl group from compound 2. To achieve this critical interconversion, the p-bromobenzoate (6) of compound 2 is prepared and then treated with thiophenol to form the bisthiophenol adduct (7). Raney nickel reduction of compound 7 will provide the desired deoxymonomer (8). Base-catalyzed coupling of compound 8 with two equivalents of compound 2 will then yield compound 1 (conocurvone).

Specific examples of chemical structures of antiviral naphthoquinone compounds, which can be isolated by the above general procedure from extracts of Conospermum plants, or which can be synthesized chemically by the above general method, are shown in FIGS. 1A–1F and, in addition to conocurvone (1), include compounds 4 and 9. A synthesis method for compound 10 was previously reported in the literature (Jurd, L., Aust. J. Chem., 33: 1603–1610, 1980). However, the antiviral activity of compound 10 was heretofore unknown.

The proofs of the structures of compounds 1–10 of FIGS. 1A–1G can be obtained by a combination of methods, including primary spectral analyses (e.g., high-resolution NMR and mass spectrometry and infrared and UV spectroscopy), comparisons of spectral and physicochemical properties with related literature precedents, and selected derivatization and/or synthetic procedures. The structure proofs for the compounds of FIGS. 1A–1G are described in detail in Examples 2 and 3.

It will be appreciated by one who is skilled in the art that antiviral naphthoquinone compounds, other than those specifically described herein, may be isolated from other Conospermum species and other natural sources, or, that such antiviral naphthoquinone compounds may be synthesized chemically. Those skilled in the art will also appreciate that modifications in the above general procedures for isolation, purification, and synthesis may provide improved yields of active compounds. However, the critical trimeric central core, the antiviral activity of which was heretofore unknown, will be shared by all the active antiviral molecules. Accordingly, the present invention is directed to series of such antiviral trimeric naphthoquinone compounds. Generic structural series (A–D) of antiviral, trimeric naphthoquinone compounds are described in detail in Example 4A–D and set forth in FIG. 4.

The activity of the pure antiviral naphthoquinone compounds can be further demonstrated in a series of interrelated in vitro antiviral assays (Gulakowski, R. J., et al., *J. Virol. Methods*, 33: 87–100, 1991), which accurately predict antiviral activity of chemical compounds in humans. These assays measure the ability of compounds to prevent the replication of HIV and/or the cytopathic effects of HIV on human target cells. These measurements directly correlate with the pathogenesis of HIV-induced disease in vivo. Accordingly, the results of the analysis of the antiviral activity of naphthoquinone compounds, as set forth in Example 5 and as illustrated in FIG. 5, are believed to predict accurately the antiviral activity of these compounds in humans.

The compounds of the present invention can be shown to inhibit a retrovirus, such as the human immunodeficiency virus, specifically HIV-1 or HIV-2. As one skilled in the art will appreciate, the compounds of the present invention probably will inhibit other retroviruses and may inhibit viruses, other than retroviruses. Examples of viruses that may be treated in accordance with the present invention include, but are not limited to, Type C and Type D retroviruses, HTLV-1, HTLV-2, HIV, FLV, SIV, MLV, BLV, BIV, equine infections, anemia virus, avian sarcoma viruses, such as Rous sarcoma virus (RSV), hepatitis type A, B, non-A and non-B viruses, arboviruses, varicella viruses, measles, mumps and rubella viruses.

The antiviral naphthoquinones, derivatives thereof, and/or prodrugs thereof, may be formulated into various compositions for use in therapeutic and prophylactic treatment methods. One skilled in the art will appreciate that prodrug forms of the antiviral naphthoquinones of the present invention may be readily prepared and may have advantageous physicochemical properties in therapeutic compositions. For example, antiviral naphthoquinone prodrugs having enhanced water-solubility (e.g., which are better for parenterally-administered compositions) may be prepared by chemical reduction of the quinonic functionalities to the corresponding quinols, followed by reaction with phosphorous oxychloride to give the corresponding phosphoric acid esters. After in vivo administration of a composition containing such a solubilized antiviral naphthoquinone prodrug, the prodrug will be readily hydrolyzed to the corresponding quinol, which thereafter will oxidize to re-form in vivo the active parent antiviral naphthoquinone. Likewise, other kinds of derivatives may be prepared from the reduced quinol derivatives of the antiviral naphthoquinones; these can also serve as prodrugs with other advantageous properties for use in therapeutic compositions. For example, other types of esterification (e.g., acetylation) may be used to produce antiviral naphthoquinone prodrugs with enhanced lipophilicity; this could promote passage of the prodrug into the central nervous system, after which it would be hydrolyzed and oxidized to its parent active antiviral naphthoquinone compound. This would be of particular value in patients having HIV infection of the central nervous system.

The present inventive composition may be used to treat a virally infected animal, such as a human. The compositions of the present invention are particularly useful in inhibiting the growth or replication of a virus, such as a retrovirus, in particular a human immunodeficiency virus, specifically HIV-1 and HIV-2. The compositions also are expected to be useful in the treatment of animals, such as humans, infected with other viruses, such as those listed above. Furthermore, such compositions should find utility in the prophylactic treatment of animals, such as humans, who are at risk for viral infection.

Compositions for use in the prophylactic or therapeutic treatment methods of the present invention comprise one or more antiviral naphthoquinones, derivatives thereof, and/or prodrugs thereof, and a pharmaceutically acceptable carrier. Pharmaceutically acceptable carriers are well-known to those who are skilled in the art, as are suitable methods of administration. The choice of carrier will be determined in part by the particular naphthoquinone compound, as well as by the particular method used to administer the composition.

One skilled in the art will appreciate that various routes of administering a drug are available, and, although more than one route may be used to administer a particular drug, a particular route may provide a more immediate and more effective reaction than another route. Furthermore, one skilled in the art will appreciate that the particular pharmaceutical carrier employed will depend, in part, upon the particular compound employed and the chosen route of administration. Accordingly, there is a wide variety of suitable formulations of the composition of the present invention.

Formulations suitable for oral administration may consist of liquid solutions, such as an effective amount of the compound dissolved in diluents, such as water, saline, or fruit juice; capsules, sachets or tablets, each containing a predetermined amount of the active ingredient, as solid or granules; solutions or suspensions in an aqueous liquid; and oil-in-water emulsions or water-in-oil emulsions. Tablet forms may include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers.

The antiviral naphthoquinones, derivatives thereof, and/or prodrugs thereof, alone or in combination with other antiviral compounds, can be made into aerosol formulations to be administered via inhalation. These aerosol formulations can be placed into pressurized acceptable propellants, such as dichlorodifluoromethane, propane, nitrogen, and the like.

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams,emulsions, gels, and the like containing, in addition to the active ingredient, such carriers as are known in the art.

Formulations for rectal administration may be presented as a suppository with a suitable base comprising, for example, cocoa butter or a salicylate. Formulations suitable for vaginal administration may be presented as pessaries, tampons, creams, gels, pastes, foams, or spray formulas containing, in addition to the active ingredient, such carriers as are known in the art to be appropriate. Similarly, the active ingredient may be combined with a lubricant as a coating on a condom.

Formulations suitable for parenteral administration include aqueous and non-aqueous, isotonic sterile injection solutions, which may contain anti-oxidants, buffers, bacteriostats, and solutes that render the formulation isotonic with the blood of the intended recipient, and aqueous and non-aqueous sterile suspensions that may include suspending agents, solubilizers, thickening agents, stabilizers, and preservatives. The formulations may be presented in unit-dose or multi-dose sealed containers, such as ampules and vials, and may be stored in a freeze-dried (lyophilized) condition requiring only the addition of the sterile liquid carrier, for example, water, for injections, immediately prior to use. Extemporaneous injection solutions and suspensions may be prepared from sterile powders, granules, and tablets of the kind previously described.

The dose administered to an animal, particularly a human, in the context of the present invention should be sufficient to effect a prophylactic or therapeutic response in the infected individual over a reasonable time frame. The dose will be determined by the potency of the particular naphthoquinone compound employed, the severity of the disease state, as well as the body weight and age of the infected individual. The size of the dose also will be determined by the existence of any adverse side effects that may accompany the particular compound employed. It is always desirable, whenever possible, to keep adverse side effects to a minimum.

The dosage may be in unit dosage form, such as a tablet or capsule. The term "unit dosage form" as used herein refers to physically discrete units suitable as unitary dosages for human and animal subjects, each unit containing a predetermined quantity of naphthoquinone compound(s), alone or in combination with other antiviral agents, calculated in an amount sufficient to produce the desired effect in association with a pharmaceutically acceptable diluent, carrier, or vehicle.

The specifications for the unit dosage forms of the present invention depend on the particular compound or compounds employed and the effect to be achieved, as well as the pharmacodynamics associated with each compound in the host. The dose administered should be an "antiviral effective amount" or an amount necessary to achieve an "effective level" in the individual patient.

Since the "effective level" is used as the preferred endpoint for dosing, the actual dose and schedule may vary, depending upon interindividual differences in pharmacokinetics, drug distribution, and metabolism. The "effective level" may be defined, for example, as the blood or tissue level desired in the patient that corresponds to a concentration of one or more naphthoquinone compound(s), which inhibits a virus, such as HIV, in an assay known to predict for clinical antiviral activity of chemical compounds. The "effective level" for compounds of the present invention also may vary when the compositions of the present invention are used in combination with AZT or other known antiviral compounds or combinations thereof.

One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effective concentration" of the compounds of the present invention by a direct (e.g., analytical chemical analysis) or indirect (e.g., with surrogate indicators such as p24 or RT) analysis of appropriate patient samples (e.g., blood and/or tissues).

In the treatment of some virally infected individuals, it may be desirable to utilize a "mega-dosing" regimen, wherein a large dose of the naphthoquinone, derivative thereof, and/or prodrug thereof is administered, time is allowed for the compound to act, and then a suitable reagent is administered to the individual to inactivate the naphthoquinone compound.

The pharmaceutical composition may contain other pharmaceuticals, in conjunction with the naphthoquinone, derivative, and/or prodrug, when used to therapeutically treat acquired immunodeficiency syndrome (AIDS). Representative examples of these additional pharmaceuticals include antiviral compounds, immunomodulators, immunostimulants, and antibiotics. Examples of antiviral compounds include AZT, ddI, ddC, gancylclovir, fluorinated dideoxy-nucleotides, nonnucleoside analog compounds such as nevirapine (Shih et al., *PNAS*, 88: 9878–9882, 1991), TIBO derivatives such as R82913 (White et al., *Antiviral Research*, 16: 257–266, 1991), and BI-RJ-70 (Shih et al., *Am. J. Med.*, 90 (Suppl. 4A): 8S-17S, 1991). Exempletive immunomodulators and immunostimulants include various interleukins, CD4, cytokines, antibody preparations, blood transfusions, and cell transfusions. Exempletive antibiotics include antifungal agents, antibacterial agents, and anti-Pneumocystitis carnii agents.

Administration of the virus-inhibitory naphthoquinone compound with other anti-retroviral agents and particularly with known RT inhibitors, such as ddC, AZT, ddI, ddA, or other inhibitors that act against other HIV proteins, such as anti-TAT agents, will generally inhibit most or all replicative stages of the viral life cycle. The dosages of ddC and AZT used in AIDS or ARC patients have been published. A virustatic range of ddC is generally between 0.05 μM to 1.0 μM. A range of about 0.005–0.25 mg/kg body weight is virustatic in most patients. The preliminary dose ranges for oral administration are somewhat broader, for example 0.001 to 0.25 mg/kg given in one or more doses at intervals of 2, 4, 6, 8, 12, etc. hours. Currently, 0.01 mg/kg body weight ddC given every 8 hrs is preferred. When given in combined therapy, the other antiviral compound, for example, may be given at the same time as the naphthoquinone compound or the dosing may be staggered as desired. The two drugs also may be combined in a composition. Doses of each may be less when used in combination than when either is used alone.

The present inventive compounds and methods are further described in the context-of the following examples. These examples serve to illustrate further the present invention and are not intended to limit the scope of the invention.

EXAMPLE 1

This example illustrates the isolation and purification of an antiviral naphthoquinone compound of the present invention, specifically conocurvone (1), from extracts of a plant known as Conospermum sp. (Spjut 7139).

Dried plant material (1,287 g) was ground, percolated in 1:1 $CH_2Cl_2$/MeOH and then washed with 100% MeOH. Solvent was removed in vacuo to provide a total of 39.0 g of crude organic extract.

An 11.53 g portion of the crude extract was suspended in 450 ml of a 9:1 MeOH/$H_2O$ mixture and partitioned with hexane (4×300 ml) to yield 2.72 g of hexane-soluble material. Addition of 45 ml of $H_2O$ to the aqueous methanol layer and subsequent partitioning with $CCl_4$ (4×300 ml) afforded 1.00 g (8.7% of the crude extract) of anti-HIV active $CCl_4$ solubles. The hexane-soluble fraction was defatted by a repeat of the partitioning between hexane (800 ml) and 9:1 MeOH/$H_2O$ (800 ml) to give an additional active methanol fraction (0.60 g, 5.2% of the crude extract).

Both active fractions were subjected to high-speed countercurrent liquid-liquid chromatography, using an Ito Multi Layer Coil apparatus (P.C. Inc., Potomac, Md.) equipped with a 2.6 mm inner diameter coil (volume 375 ml). The rotational speed was 800 rpm and a biphasic solvent system composed of hexane/EtOH/EtOAc/$H_2O$ (5:4:2:1) was pumped at an initial flow rate of 1 ml/minute at the time of sample injection and then gradually increased to 2 ml/minute for the remainder of the run. The chromatograph was operated in the ascending mode with the upper organic layer used as the mobile phase. Samples were first dissolved in a mixture of the two-phase solvent system and injected in 4 portions of 8–10 ml each. The separation was monitored using a Linear Instruments UV detector model UV 200 measuring at 280 nm. All fractions were also analyzed by TLC (Rf=0.08) on silica gel 60 $F_{254}$ (EM Sciences) with the organic mobile phase as the developing solvent.

Active fractions from the countercurrent chromatography (245 mg total) were further separated by low-pressure liquid chromatography on diol packing (LiChroprep DIOL, 40–63 µm, EM Sciences) using a 25×310 mm column and gradient elution of hexane/EtOAc from 99:1 to 7:3. The flow rate was gradually increased from 0.5 to 3.5 ml/minute and the separation was monitored at 280 nm as previously described to give 23.8 mg of active material.

Final purification of the active component was achieved by HPLC on a phenyl bonded phase column (Rainin Dynamax-60A, 8 µm, 4.6 mm I.D.×25 cm). The eluting solvent, delivered at a flow rate of 1.0 ml/minute, was composed of $CH_3CN/H_2O$ (17:3, 0.1% HOAc by vol). The samples were dissolved in a mixture of 500 µl $CH_2Cl_2$ plus 750 µl $CH_3CN$ and the injection volume was 75–100 µl. The separations were monitored with a Waters 990 photodiode array detector at 210 nm. This final purification step yielded a total of 8.5 mg (0.07% of the crude extract) of conocurvone (1) with a HPLC retention time of 29 minutes. Rf=0.38 on CN TLC $F_{254}$ (EM Science) with hexane/IPA (8:2) plus 1% acetic acid; Rf=0.47 on diol $F_{254}$ (EM Science) with hexane/IPA (8:2) plus 1% acetic acid; and Rf=0.32 on RP-8 $F_{254}$ (EM Science) with $MeOH/H_2O$ (95:5) plus 1% acetic acid.

Spectral and physicochemical properties recorded for pure compound 1 were as follows: $[\alpha]_D+184°$ (MeOH, c 0.32);

UV $\lambda_{max}$ (MeOH) 225 nm (log $\epsilon$=4.9), 275 (4.6), 289 (4.6), 405 (4.2); IR (film) $v_{max}$ 2969, 2922, 2857, 1657, 1650, 1644, 1563, 1462, 1287, 1207, 1076, 1005, 915, 866, 750 cm$^{-1}$; positive-ion FAB-MS m/z 953.3856 (MH+, calc'd for $C_{60}H_{57}O_{11}$ 953.3901), with a linked scan providing daughter ions at m/z 871.3073 (calc'd for $C_{54}H_{47}O_{11}$ 871.3118) and 869.2957 (calc'd for $C_{54}H_{45}O_{11}$ 869.2962); negative ion FAB-MS m/z 952.3872 (M−, calc'd for $C_{60}H_{56}O_{11}$ 952.3823), with a linked scan providing daughter ions at m/z 629.2535 (calc'd for $C_{40}H_{37}O_7$ 629.2539) and m/z 323.1281 (calc'd for $C_{20}H_{19}O_4$ 323.1283); LR negative-ion FAB-MS using a matrix of nitrobenzyl alcohol, deuterated glycerol and deuterated MeOH gave m/z 954 and daughter ions at m/z 630 and m/z 324; and $^1$H NMR (CDCl$_3$) δ 1.39–1.42 (a series of overlapped CH$_3$ singlets, which integrated for 9H), 1.50–1.56 (a series of overlapped CH$_3$ singlets, which integrated for 9H), 1.61–1.65 (a series of overlapped CH$_3$ singlets, which integrated for 9H), 1.63–1.70 (m, 3H), 1.71–1.79 (m, 3H), 2.03–2.11 (m, 6H), 5.01–5.09 (m, 3H), 5.81–5.83 (overlapped doublets, J=10.5, which integrated for 1H), 5.89–5.92 (overlapped doublets, J=10.5, which integrated for 2H), 6.99–7.09 (overlapped doublets, J=8.5, which integrated for 3H), 7.51–7.63 (OH, exchangeable, integrated for 2H), 7.71–7.76 (overlapped doublets, J=10.5, which integrated for 3H), and 7.89–8.01 (overlapped doublets, J=8.5, which integrated for 3H).

Using a modification of the previously published isolation procedure (Cannon, J. R., et al., *Tetrahedron Lett.*, 2795–2798, 1975), teretifolione B (2) was reisolated from an extract of Conospermum sp. In brief, compound 2 was isolated by partitioning the extract between $CH_2Cl_2$ and a 7:3 mixture of $MeOH/H_2O$, conducting a gel permeation of the $CH_2Cl_2$ solubles on Sephadex LH-20 with 1:1 $CH_2Cl_2$/MeOH, carrying out low pressure column chromatography on diol packing eluting with increasingly polar mixtures of hexane/EtOAc and $C_{18}$ HPLC, using $MeOH/H_2$(19:1, 0.1% HOAc by vol). This compound (2) had been previously reported as one of a series of quinones isolated from *Conospermum teretifolium* (Cannon, J. R., et al., *Tetrahedron Lett.*, 2795–2798, 1975). While the structure of compound 2 was originally verified by synthesis (Cannon, J. R., et al., *Tetrahedron Lett.*, 2795–2798, 1975), no NMR, UV or IR data were provided for the compound. The independent spectrochemical characterization of teretifolione B (2), as now provided herein, confirmed the structure, and proton-detected heteronuclear correlation experiments (HMQC and HMBC) allowed the complete assignment of all $^1$H and $^{13}$C NMR resonances.

Spectral and physicochemical properties recorded for pure compound 2 were as follows: $[\alpha]_D66°$ (MeOH, c 0.1); UV $\lambda_{max}$ (MeOH) 215 nm (log $\epsilon$=4.7), 291 (4.3), 394 (3.8); IR (film) $v_{max}$ 3350 (broad), 2970, 2926, 1660, 1651, 1639, 1563, 1463, 1311, 1207, 1074, 972, 844, 744 cm$^-$; positive-ion FAB-MS m/z 325.1435 (MH+, calc'd for $C_{20}H_{21}O_4$ 325.1440); $^{13}$C NMR (125 MHz, CDCl$_3$, # attached H from DEPT experiment) δ 183.9 (C-1, 0), 156.5 (C-2, 0), 109.0 (C-3, 1), 184.4 (C-4, 0), 126.9 (C-4a, 0), 128.6 (C-5), 122.1 (C-6, 1), 158.1 (C-7, 0), 121.5 (C-8, 0), 123.3 (C-8a, 0), 119.9 (C-9, 1), 135.4 (C-10, 1), 79.3 (C-11, 0), 41.2 (C-12, 2), 22.6 (C-13, 2), 123.4 (C-14, 1), 132.1 (C-15, 0), 25.5 (C-16, 3), 17.5 (C-17, 3), 26.5 (C-18, 3); and $^1$H NMR (500 MHz, CDCl$_3$) δ 1.40 (H-18, Me, s), 1.51 (H-17, Me, s), 1.60 (H-16, Me, s), 1.65 (H-12', m), 1.74 (H-12, m), 2.05 (H-13, 2H, m), 5.03 (H-14, m), 5.90 (H-10, d, J=10.5), 6.21 (H-3, s), 7.04 (H-6, dd, J=8.5, 0.7), 7.48 (OH, exchangeable), 7.76 (H-9, dd, J=10.5, 0.7), 7.90 (H-5, d, J=8.5).

EXAMPLE 2

This example sets out the structure proof for an antiviral naphthoquinone compound of the present invention, specifically conocurvone (1).

Figure 2A:
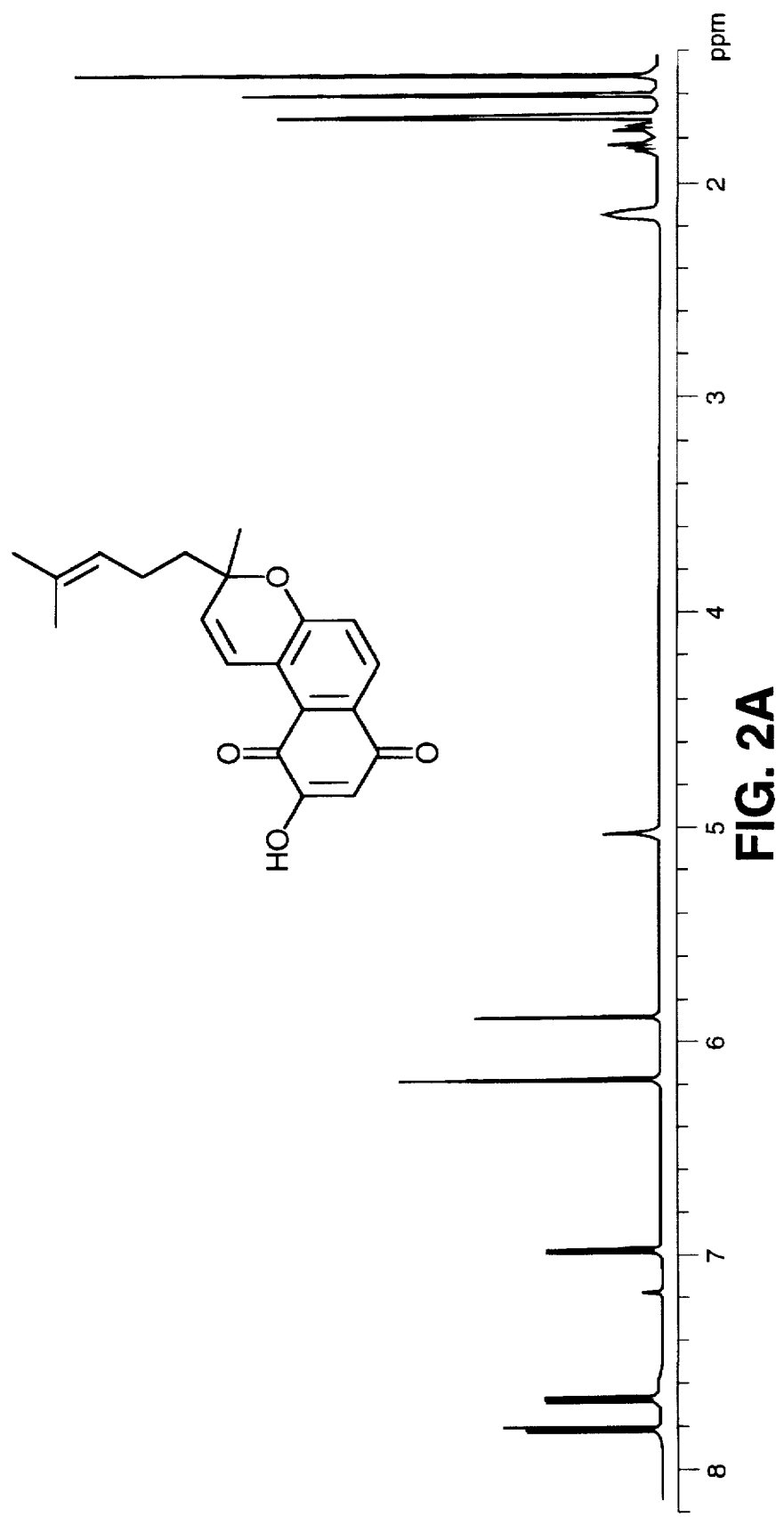
FIG. 2 shows 500 MHz $^1$H NMR spectra (CDCl$_3$) of (A) the monomer teretifolione B (2), (B) the naturally occurring trimer conocurvone (1), and (C) a semi-synthetic derivative (4).
Figure 2B:
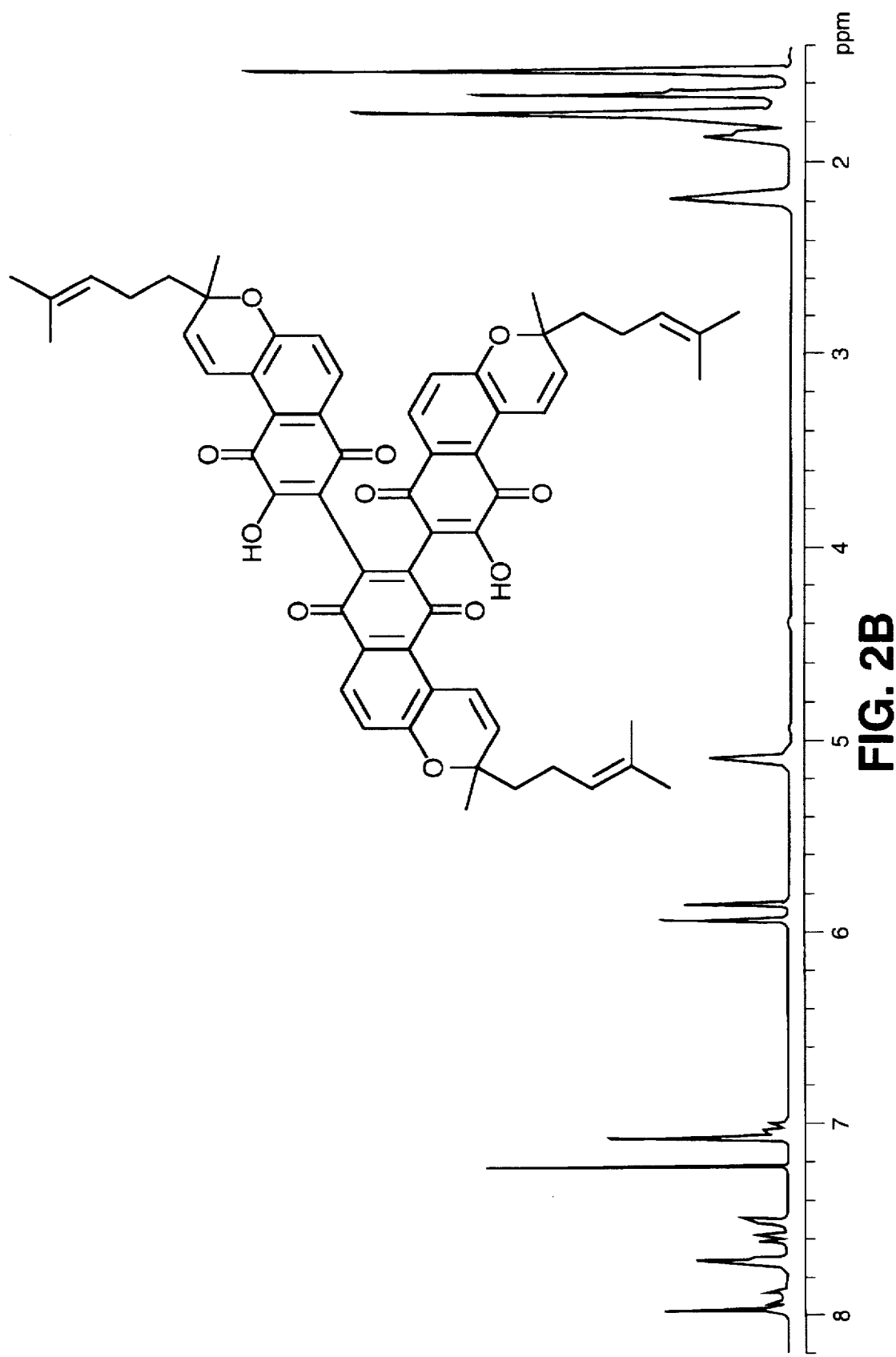
Figure 2C:
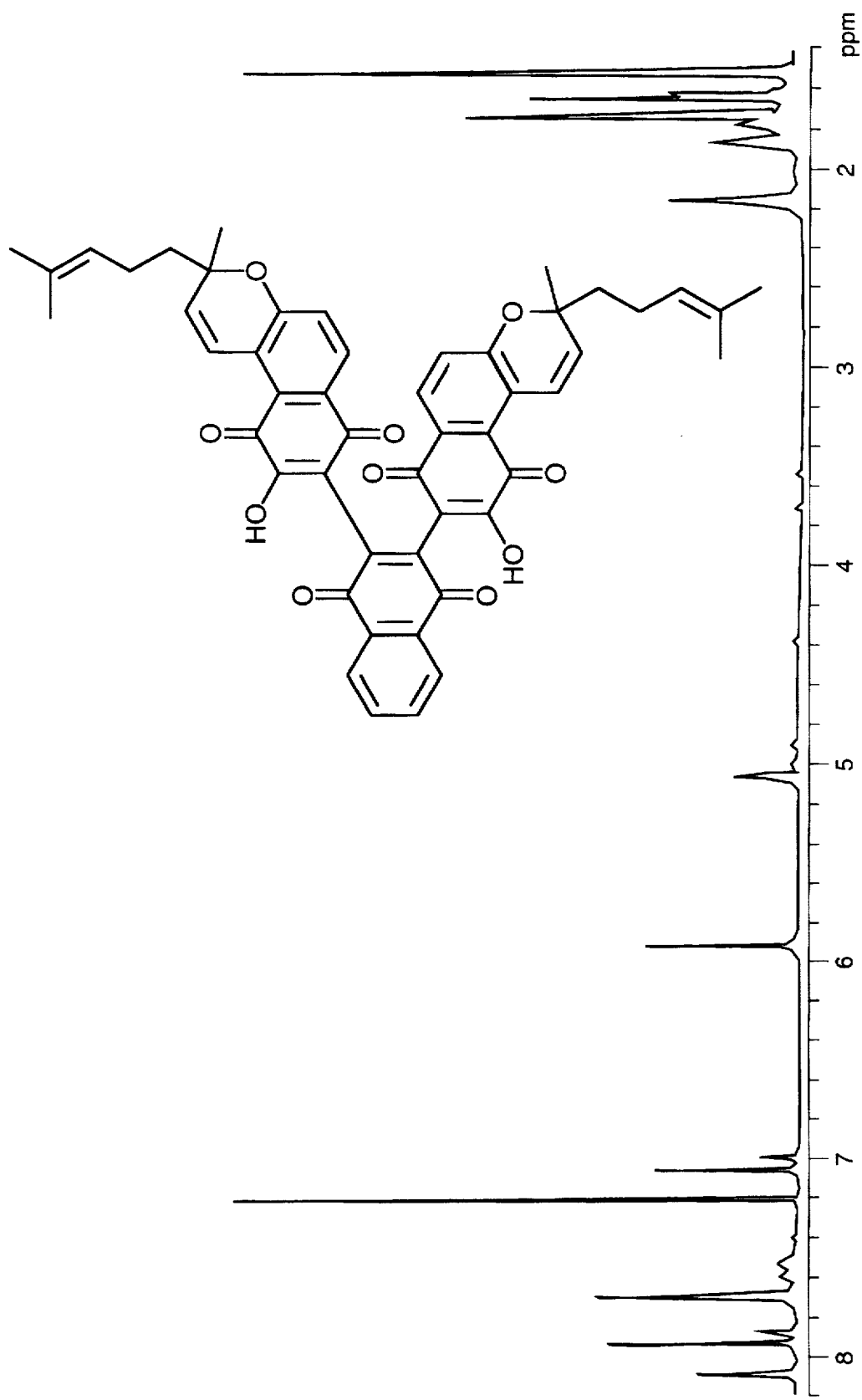

The $^1$H NMR spectrum of conocurvone was very complex, with many highly overlapped resonances (FIG. 2). In addition, the aromatic proton resonances (FIG. 3) were flanked by satellite peaks that apparently integrated for less than one proton. The satellite peaks were originally suspected to arise from a chromatographically inseparable impurity that co-eluted with conocurvone. However, the complexity and chemical shifts of both the major $^1$H NMR signals and the satellite resonances varied, depending on the deuterated solvent used and the temperature of the sample. Spectra were acquired and analyzed in CDCl$_3$, CD$_3$OD, CD$_3$CN, DMSO-d$_6$, pyridine-d$_5$ and benzene-d6. Benzene-d$_6$ provided the most complex proton NMR spectrum, while CDCl$_3$ gave the least complex spectrum. Neither heating the sample to 100° nor cooling to −40° eliminated the satellite peaks, although significant changes in the appearance and coupling patterns of the major and minor signals were evident. In addition to changes in spectral complexity, changes in the relative integration of the major signals and satellite peaks were also observed in the different NMR solvents and at varying temperatures. These observations suggested that the conocurvone (1) sample was indeed pure and that the satellite peaks and much of the spectral complexity arose from a dynamic intramolecular process, such as tautomerization and/or restricted rotation about one or more bonds in the molecule, which was observable on the NMR time scale.

While the $^1$H NMR spectrum of conocurvone (1) was complex, it exhibited many similarities to the spectrum of teretifolione B (2). The $^{13}$C NMR spectrum of compound 1 also showed close correspondence to that recorded for compound 2, but many of the resonances occurred as overlapping clusters of peaks. The structure of conocurvone (1) was clearly related to that of teretifolione B (2), but the complex nature of the NMR data for compound 1 prevented a complete and straightforward structural elucidation by conventional NMR analysis. Key information on the nature of compound 1 was obtained from mass spectroscopic studies. High-resolution FAB MS in both the positive- and negative-ion ion modes revealed a unique molecular formula for compound 1 of $C_{60}H_{56}O_{11}$. In the positive-ion mode, a pseudomolecular ion was observed at m/z 953.3856 for MH+ ($C_{60}H_{57}O_{11}$), while negative-ion FAB MS revealed a molecular ion at m/z 952.3872 for M- ($C_{60}H_{56}O_{11}$) and daughter ions in a linked scan at m/z 629.2535 for $C_{40}H_{37}O_7$ and m/z 323.1281 for $C_{20}H_{19}O_4$. Negative-ion FAB MS using a matrix of nitrobenzyl alcohol, deuterated glycerol and deuterated methanol produced a peak at m/z 954, which revealed that conocurvone (1) contained two exchangeable hydrogen atoms. A linked scan analysis provided daughter ions at m/z 630 and 324, indicating that these fragments each contained one exchangeable hydrogen. The molecular formula, mass spectral fragmentation pattern, and NMR spectral features indicated that conocurvone (1) has a non-symmetrical trimeric structure containing three quinone subunits structurally related to compound 2.

It was surmised that conocurvone (1) consisted of two teretifolione B subunits joined at their C3 positions to the C2 and C3 positions of a 2-deoxyteretifolione B subunit. Structure 1 is consistent with the observed mass spectral data and would be expected to exhibit the effects of both tautomerism and restricted rotation. The two hydroxyquinone functionalities in the molecule can exist in either the ortho or para quinone forms. The relative distribution of the ortho and para quinones and their rate of interconversion could vary with changes in both solvent and temperature. The planar orientation of the quinones in the two teretifolione B subunits is likely to be nearly orthogonal to the plane of the quinone in the central 2-deoxyteretifolione B portion of the molecule. Molecular models revealed that, although it is hindered, rotation about the bonds joining the two teretifolione B subunits to the central 2-deoxyteretifolione B subunit should be possible. Since each subunit in compound 1 is unsymmetrical and contains a chiral carbon, there are 4 different tautomeric forms and 4 different rotational atropisomers possible. In combination, this means that conocurvone, (1) can theoretically exist in, and interconvert among, a total of 16 different forms. The occurrence of, and NMR effects due to, similar types of ketoenol tautomerism and restricted rotation about the bonds joining subunits of other dimeric and "trimeric" naphthoquinone derivatives are well known (Waterman, P. G., et. al., *J. Chem. Res.*, (M) 0101–0144, 1985; Jeffreys, J. A. D., et al., *Tetrahedron Lett.*, 1085–1088, 1983; Durley, R. C., et al., *J. Chem. Soc. Perkin I*, 153–169, 1975). The present data, therefore, are fully consistent with the spectral characteristics that have been reported for these types of compounds.

Acetylation of conocurvone (1) with acetic anhydride in pyridine, followed by phenyl bonded phase HPLC of the reaction product, provided a chromatogram with one main peak and many smaller peaks. A 5.2 mg sample of conocurvone (1) was stirred at room temperature for 24 hr in 1 ml pyridine and 1 ml acetic anhydride. Ten ml of EtOAc were added to the reaction mixture, which was then washed successively with a 10% $CuSO_4$ solution and 3× with $H_2O$. The EtOAc layer was dried over anhydrous $Na_2SO_4$ and evaporated to give 5.2 mg of product, which gave a single spot by TLC on silica plates developed with $CHCl_3$/MeOH (9:1). HPLC on a phenyl bonded phase column with $CH_3CN$/$H_2O$ (19:1) provided a chromatogram with a series of peaks. The principal peak was collected (2.1 mg), but it gave a complex $^1H$ NMR spectrum. Reinjection of the material collected as the principal peak gave one major peak and three minor ones. The material collected as the major peak of the second HPLC separation still gave a complex $^1H$ NMR spectrum, and when reanalyzed under the exact same HPLC conditions, it again gave a chromatogram with one main peak and three minor ones. Photodiode array detection of the HPLC eluant showed that all four peaks had similar UV absorption profiles with a $\lambda_{max}$ at 230 and a shoulder at 273 nm. The HPLC-purified acetylation product gave a LRMS molecular ion at m/z 1036; $^1H$ NMR ($CDCl_3$) δ 1.39–1.44 (a series of overlapped $CH_3$ singlets, which integrated for 9H), 1.53–1.58 (a series of overlapped $CH_3$ singlets, which integrated for 9H), 1.62–1.66 (a series of overlapped $CH_3$ singlets, which integrated for 9H), 1.61–1.71 (m, 3H), 1.72–1.81 (m, 3H), 2.01–2.10 (m, 6H), 2.09–2.12 (a series of overlapped $CH_3$ singlets, which integrated for 6H), 5.06 (m, 3H), 5.80–5.85 (overlapped doublets, J=10.5, which integrated for 3H), 7.03–7.09 (overlapped doublets, J=9.0, which integrated for 3H), 7.60–7.64 (overlapped doublets, J=10.5, which integrated for 2H), 7.72–7.75 (overlapped doublets, J=10.5, which integrated for 1H), 7.90–7.92 (overlapped doublets, J=9.0, which integrated for 2H), 7.99–8.01 (overlapped doublets, J=9.0, which integrated for 1H). Thus, while acetylation of the two hydroxyl groups in compound 1 would eliminate tautomeric interconversions, these results indicated that the acetate groups were not sufficiently bulky to block rotation about the bonds joining the three quinone subunits.

In an effort to fully eliminate the effects of tautomerism and rotational interconversions, conocurvone (1) was reductively acetylated using an adaptation of published methodology (Cameron, D. W., and Siddel, M. D., *Aust. J. Chem.*, 31: 1323–1333, 1978). A 6.3 mg aliquot of conocurvone (1) in 2.5 ml acetic anhydride with 143 mg NaOAc and 168 mg Zn dust was reacted at room temperature for 3.5 hr. Cold $H_2O$ was added to the reaction mixture, which was then partitioned between $H_2O$ and $CH_2Cl_2$. The $CH_2Cl_2$ layer was dried over anhydrous $Na_2SO_4$, filtered, and the solvent removed under reduced pressure to give 9.5 mg of crude product. This material was separated by bonded phase phenyl HPLC with MeOH/$H_2O$ (19:1) to give three principal peaks. The early-eluting peak was further purified by HPLC on the chiral support cyclobond β with hexane/IPA (19:1) to give 1.1 mg of the peracetylated product 3. For compound 3: LRMS m/z 1294; $^1H$ NMR ($CDCl_3$) δ 1.20 (s, 6H), 1.35 (s, 3H), 1.57 (s, 6H), 1.61 (s, 3H), 1.66 (s, 6H), 1.70 (s, 3H), 1.71–1.79 (m, 4H), 1.82–1.88 (m, 2H), 1.95 (s, 3H), 1.96 (s, 6H), 2.0–2.13 (m, 6H), 2.08 (s, 3H), 2.20 (s, 3H), 2.24 (s, 3H), 2.33 (s, 3H), 2.34 (s, 3H), 5.10 (t, J=7.0, 2H), 5.16 (t, J=7.0, 1H), 5.54 (d, J=10.5, 1H), 5.55 (d, J=10.2, 1H), 5.65 (d, J=10.2, 1H), 6.54 (d, J=9.3, 2H), 7.12–7.22 (m, 6H), 7.62 (d, J=9.3, 1H).

Thus, compound 3 provided a molecular ion at m/z 1294 appropriate for $C_{76}H_{78}O_{13}$, and its $^1H$ NMR spectrum contained eight $CH_3$ singlets between δ 1.95–2.34 ppm due to eight acetate groups. The $^1H$ NMR signals of compound 3 were indicative of a single entity as they were sharp, less complex, and without any satellite peaks. Reductive acetylation of compound 1 provided a product that could be chromatographically purified to a homogeneous constituent with a single set of NMR resonances. No sign of rotational interconversion, as suggested by the appearance of additional HPLC peaks or NMR signals, was observed with compound 3. While the peracetate derivative 3 was a single, stable material, the rotational orientation it possessed could not be determined from its $^1H$ NMR characteristics. The lack of protonated carbons in the region of linkage between the reduced quinone subunits in the molecule made conventional analysis by heteronuclear correlation and nOe experiments problematic. The final definitive proof of the structure of conocurvone (1) isolated from Conospermum sp. (Spjut 7139) was, therefore, provided by the observations that its spectral, physicochemical, and antiviral properties were identical to those of compound 1 prepared by synthesis (see Example 3).

EXAMPLE 3

This example illustrates the synthesis of antiviral naphthoquinone compounds of the present invention, specifically conocurvone (1) and related compounds (4, 9, 10). A 61 mg aliquot of compound 2, 16 mg of 1,4-naphthoquinone, and 1 ml of glacial HOAc were stirred for 15 hr in a refluxing water bath. The mixture was taken to dryness under reduced pressure and chromatographed on Sephadex LH-20 with $CH_2Cl_2/MeOH$ (1:1). Early eluting fractions, which contained a new, more polar spot by TLC ($SiO_2$ plates developed with $CH_2Cl_2/MeOH$, 9:1, Rf=0.13), were pooled and purified by HPLC on a phenyl bonded phase column with $CH_3CN/H_2O$ (17:3, 0.1% HOAc by vol) to give 7 mg of the "trimer" 4. Later eluting fractions from the Sephadex LH-20 column were chromatographed on diol bonded phase packing to give 9 mg of compound 5. Compound 4 had the following spectral features: FAB HRMS m/z 803.2834 (MH+, calc'd for $C_{50}H_{43}O_{10}$ 803.2856); $^1H$ NMR ($CDCl_3$) δ 1.40–1.43 (a series of $CH_3$ singlets, which integrated for 6H), 1.51–1.55 (a series of $CH_3$ singlets, which integrated for 6H), 1.62–1.64 (a series of $CH_3$ singlets, which integrated for 6H), 1.64–1.71 (m, 2H), 1.73–1.81 (m, 2H), 2.04–2.11 (m, 4H), 5.03–5.08 (m, 2H), 5.91–5.93 (overlapped doublets, J=10.5, which integrated for 2H), 7.02–7.10 (overlapped doublets, J=8.5, which integrated for 2H), 7.57 (OH, exchangeable), 7.66 (OH, exchangeable), 7.73–7.76 (m, 4H), 7.93–8.01 (overlapped doublets, J=8.5, 2H), 8.14–8.16 (m, 2H). Compound 5 had the following spectral features: FAB HRMS m/z 481.1635 (MH+, calc'd for $C_{30}H_{25}O_6$ 481.1651); $^1H$ NMR ($CDCl_3$) δ 1.45 (s, 3H), 1.55 (s, 3H), 1.64 (s, 3H), 1.65–1.72 (m, 1H), 1.76–1.83 (m, 1H), 2.07–2.13 (m, 2H), 5.08 (t, J=7.0, 1H), 5.97 (d, J=10.5, 1H), 7.03 (s, 1H), 7.11 (d, J=8.5, 1H), 7.74 (m, 2H), 7.82 (d, J=10.5, 1H), 8.00 (d, J=8.5, 1H), 8.11 (m, 2H).

Figure 3A:
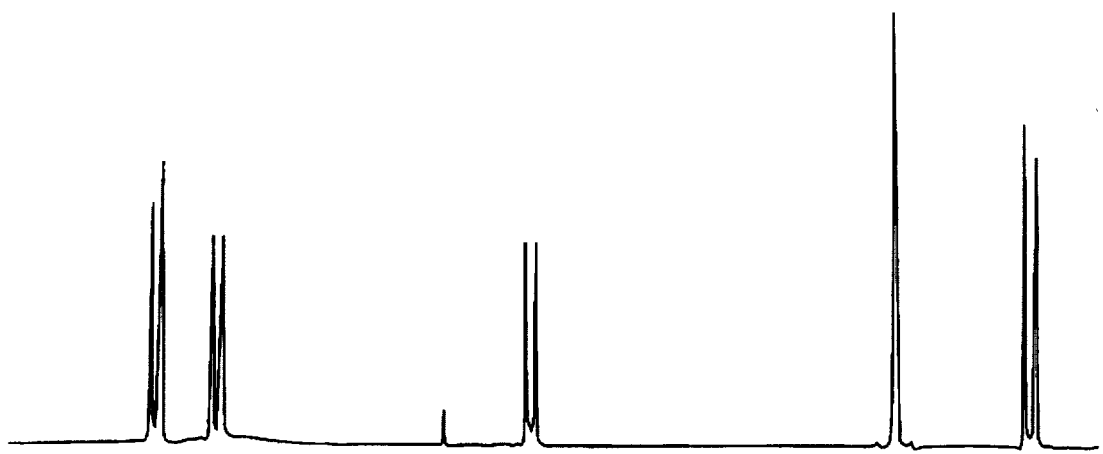
FIG. 3 illustrates expansion of the aromatic region of the 500 MHz $^1$H NMR spectra (CDCl$_3$) of (A) teretifolione B (2), (B) conocurvone (1), and (C) compound 4.
Figure 3B:
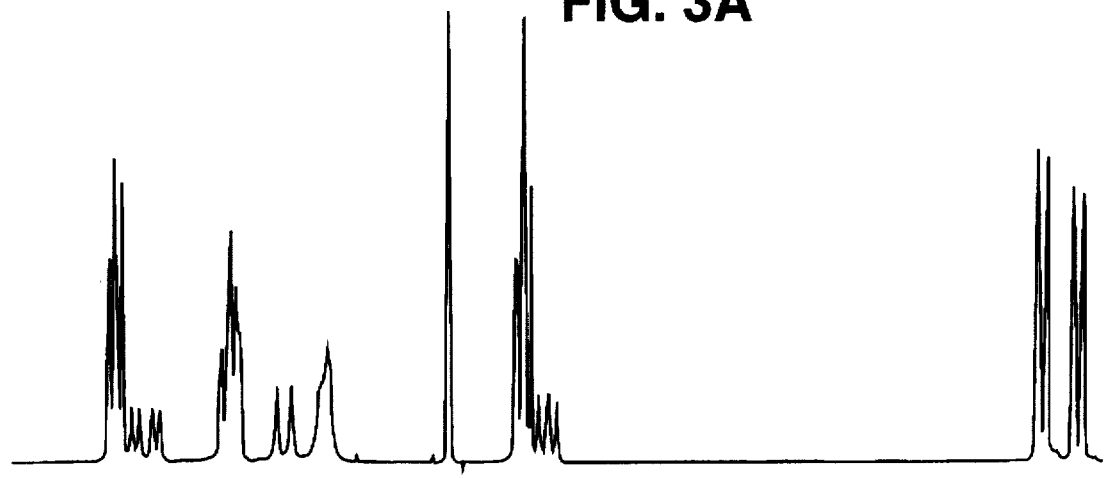
Figure 3C:
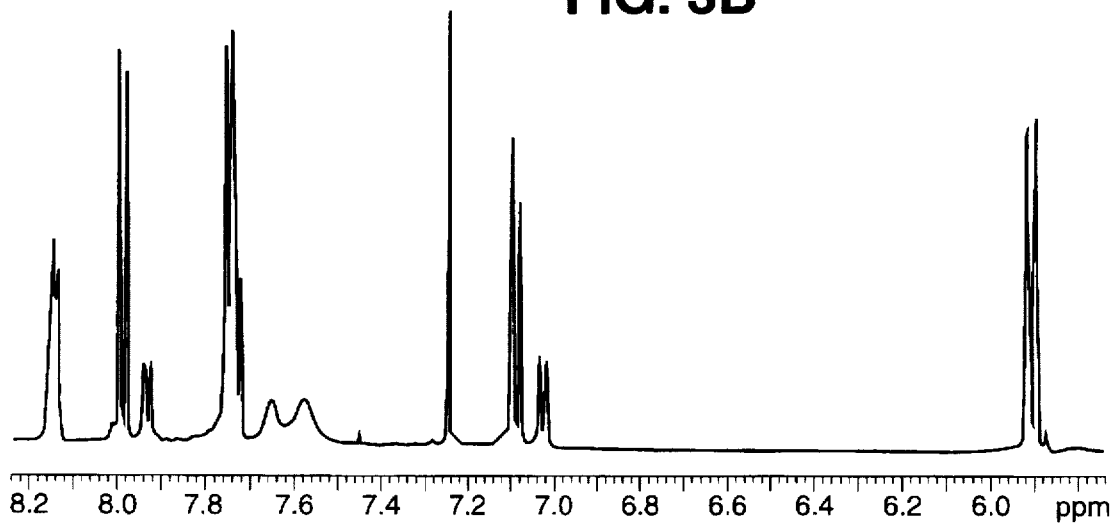
Figure 4B:
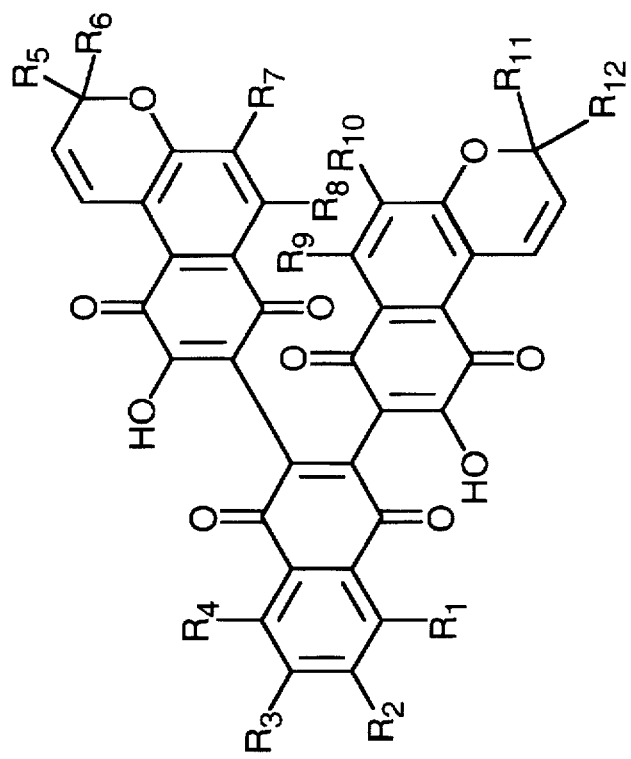
FIGS. 4A–D represents antiviral naphthoquinone compounds of series A–D respectively encompassed within the present invention, wherein $R_1$–$R_{12}$ are the same or different, and each may be H, a $C_1$–$C_{10}$ straight-chain or branched-chain, saturated or unsaturated alkyl, an aryl, OCH$_3$, or OH.
Figure 4A:
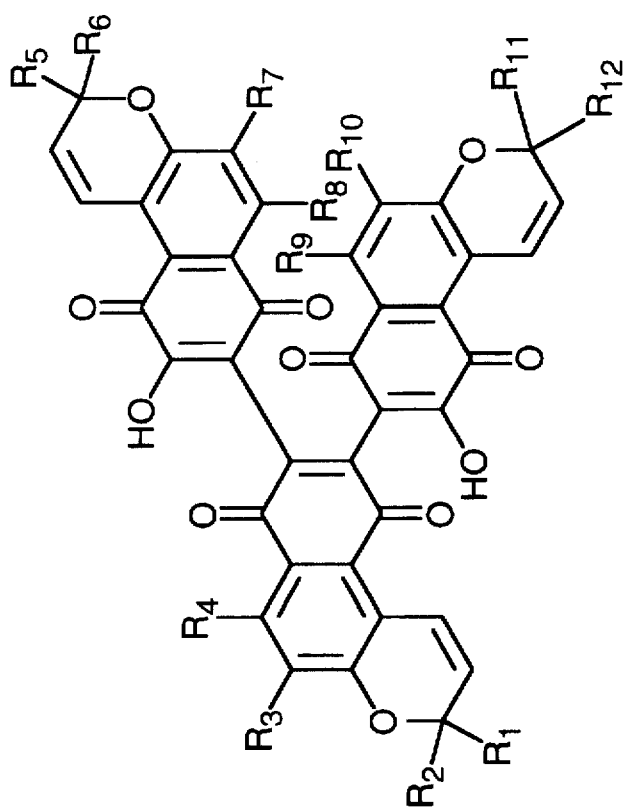
Figure 4D:
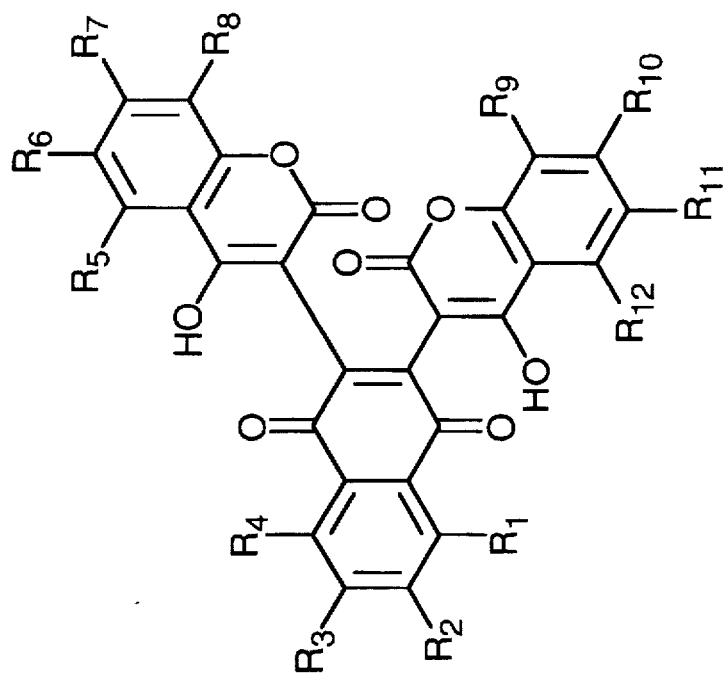
Figure 4C:
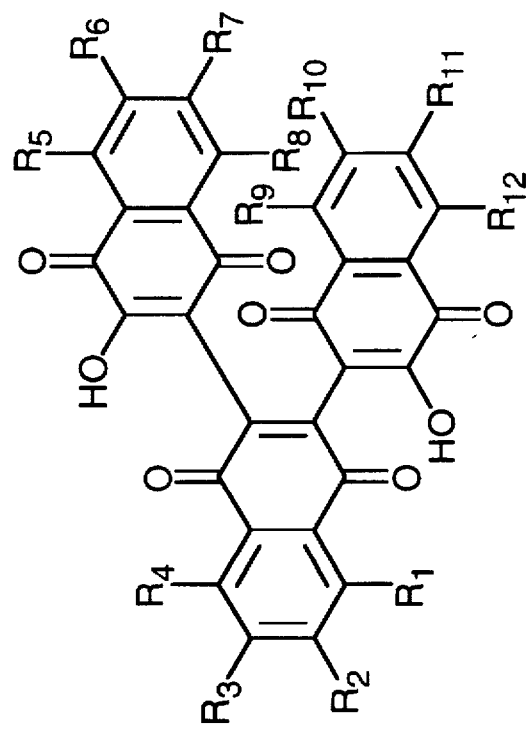
Figure 5A:
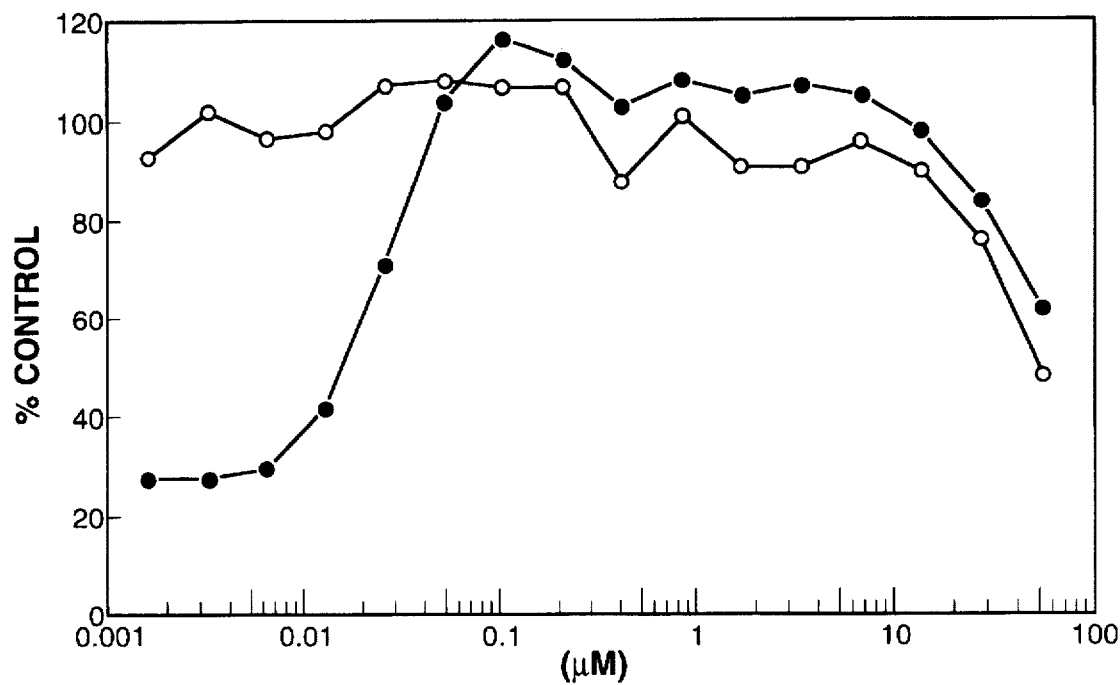
FIG. 5 illustrates an example of the antiviral activity of an antiviral naphthoquinone compound, specifically conocurvone (1). Graphs A, B, and C show the effects of a range of concentrations of conocurvone (1) upon uninfected CEM-SS cells (○) and upon CEM-SS cells infected with HIV-1 (●), as determined after 6 days in culture. Graph A depicts the relative numbers of viable CEM-SS cells, as assessed by the BCECF assay. Graph B depicts the relative DNA contents of the respective cultures. Graph C depicts the relative numbers of viable CEM-SS cells, as assessed by the XTT assay. Graph D shows the effects of a range of concentrations of conocurvone upon indices of infectious virus or viral replication as determined after 4 days in culture. These indices include viral reverse transcriptase (▲), viral core protein p24 (♦), and syncytium-forming units (■). In graphs A, B, and C, the data are represented as the percent of the uninfected, non-drug treated control values. In graph D the data are represented as the percent of the infected, non-drug treated control values.
Figure 5B:
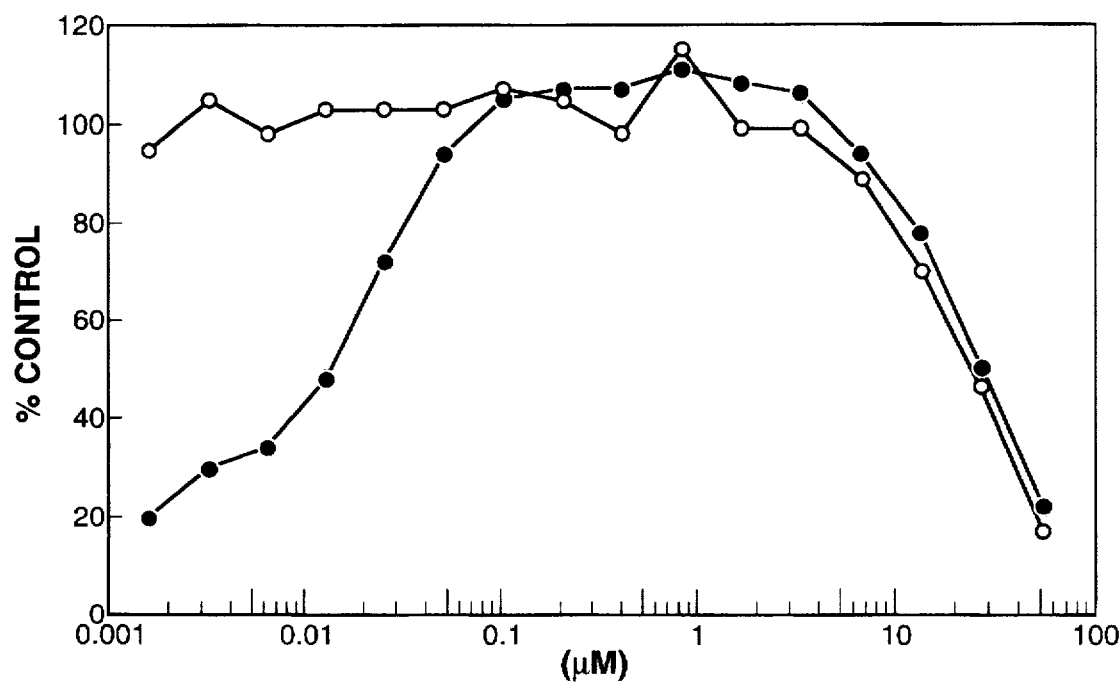
Figure 5C:
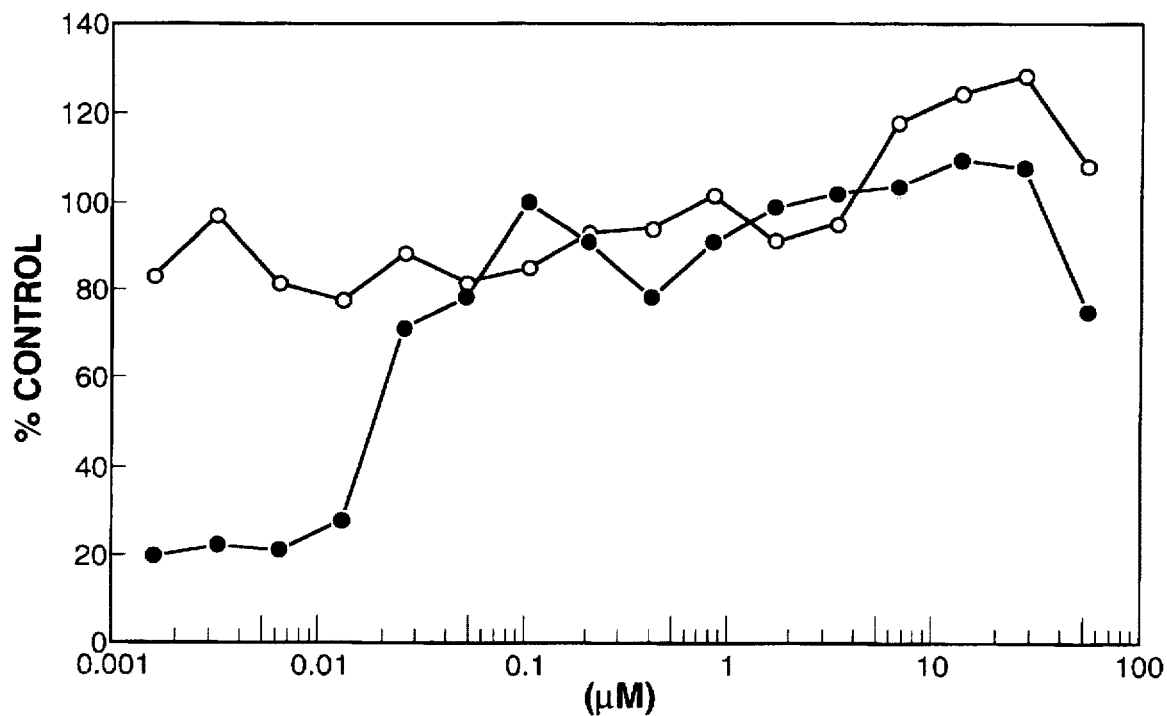
Figure 5D:
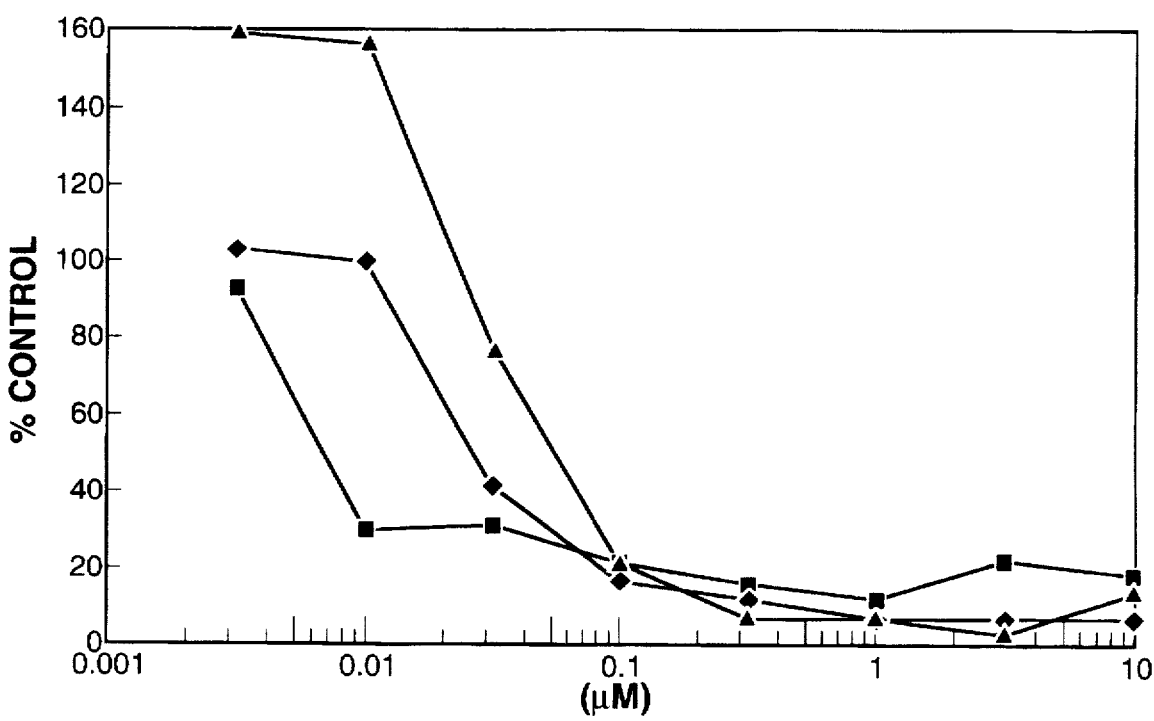

Thus, the "trimer" 4 had $^1H$ NMR characteristics which were very similar to those of conocurvone (1) (see FIGS. 2 and 3). The $^1H$ NMR resonances of compound 4 were complex, with many highly overlapped signals and satellite peaks. The striking similarities in the NMR spectral features of compounds 1 and 4 suggested that the same intramolecular tautomerism and rotational isomerism that had been observed in compound 1 were also occurring in compound 4. Of greater significance was the finding that the anti-HIV biological activity profile of the "synthetic trimer" 4 was virtually identical to the activity profile of conocurvone (1). In contrast, the "synthetic dimer" 5 provided sharp signals for each proton in its $^1H$ NMR spectrum and was completely inactive against HIV.

Conocurvone (1), itself, was also synthesized, using teretifolione B (2) as a precursor. The central deoxymonomeric subunit of compound 1 was produced by removal of the C2 hydroxyl group from compound 2. To achieve this critical interconversion, the p-bromobenzoate derivative 6 was treated with thiophenol to form the bisthiophenol adduct 7. Raney nickel reduction of compound 7 provided the desired deoxymonomer 8. Base-catalyzed coupling of compound 8 with two equivalents of teretifolione B (2) gave compound 1. A typical reaction sequence is as follows: teretifolione B (2; 20.7 mg) was stirred in 3 ml $CH_2Cl_2$ with 62.1 mg benzoylchloride and 1.0 ml $Et_3N$. The reaction was stopped after 15 minutes and the mixture was washed with 6×1 ml $H_2O$. The organic layer was evaporated to dryness, triturated with an EtOAc/hexane mixture and the insoluble aromatic acid filtered off. The filtrate was adsorbed onto $C_{18}$ packing and then eluted with increasing concentrations of MeOH in $H_2O$. The p-bromobenzoate derivate 6 (24.9 mg) was eluted with 95% MeOH. Compound 6 crystallized from an acetone/$H_2O$ mixture. For compound 6: electron impact HRMS m/z 506.0702 (calc'd for $C_{27}H_{23}BrO_5$ 506.0729); $^1H$ NMR ($CDCl_3$) 67 1.44 (s, 3H), 1.55 (s, 3H), 1.65 (s, 3H), 1.70 (m, 1H), 1.77 (m, 1H) 2.09 (m, 2H), 5.07 (bt, J=7.0 Hz, 1H), 5.88 (d, J=10.3 Hz, 1H), 6.79 (s, 1H), 7.01 (d, J=8.2 Hz, 1H), 7.68 (m, 2H), 7.75 (d, J=10.3 Hz, 1H), 7.98 (d, J=8.2 Hz, 1H), 8.03 (m, 2H).

Then, into 50.0 ml EtOAc was added 108 mg compound 6, 6 ml $Et_3N$, and 28 drops of thiophenol. The reaction mixture was stirred at room temperature for 1 hr and then evaporated to dryness. Step gradient vacuum-liquid chromatography (VLC) on $C_{18}$ packing provided 93.4 mg of product in the 100% MeOH fraction. Final purification by HPLC on a phenyl column with 19:1 MeOH/$H_2O$ yielded 58.4 mg of compound 7. For compound 7: electron impact HRMS m/z 524.2305 (calc'd for $C_{32}H_{28}S_2O_3$ 524.1480); IR (film) $v_{max}$ 2917, 2849, 1663, 1583, 1564, 1466, 1440, 1283, 1135 $cm^{-1}$; $^1H$ NMR ($CDCl_3$) 67 1.31 (s, 3H), 1.52 (s, 3H), 1.62 (s, 3H), 1.63 (m, 1H), 1.73 (m, 1H), 2.04 (m, 2H), 5.03 (bt, J=7.0 Hz, 1H), 5.71 (d, J=10.5 Hz, 1H), 6.95 (d, J=8.5 Hz, 1H), 7.04 (d, J=10.5 Hz, 1H) 7.22–7.31 (m, 6H), 7.35–7.37 (m, 4H), 7.78 (d, J=8.5 Hz, 1H).

Next, fresh Raney nickel was prepared by washing and sonicating commercial Raney nickel 33× with excess MeOH. 480 mg of washed Raney nickel were added to 5 ml MeOH and the solution was brought to reflux. A solution of 52.5 mg of the bisthiophenyl ether 7 in MeOH was slowly added to the refluxing Raney nickel solution. Best results were obtained by waiting for the disappearance of the red coloration before adding more of the solution containing compound 7. The reaction mixture was refluxed for a total of 1 hr, filtered, and evaporated to dryness. Purification by step gradient VLC on $C_{18}$ gave 22.6 mg of compound 8 in the 19:1 MeOH/$H_2O$ fraction. For compound 8: electron impact HRMS m/z 308.1379 (calc'd for $C_{20}H_{20}O_3$ 308.1412); UV $\lambda_{max}$ (MeOH) 225 nm (log ε=4.4), 298 (3.7), 429 (3.5); IR (film) $v_{max}$ 2965, 2923, 2853, 1655, 1611, 1576, 1562, 1458, 1437, 1300, 1192 $cm^{-1}$; $^{13}C$ NMR ($CDCl_3$, assignments made from HMQC, HMBC and DEPT experiments) δ 188.0 (C-1), 140.0 (C-2*), 137.3 (C-3*), 184.3 (C-4), 126.2 (C-4a), 128.8 (C-5), 121.2 (C-6), 159.2 (C-7), 120.7 (C-8), 129.3 (C-8a), 120.1 (C-9), 134.2 (C-10), 79.5 (C-11), 41.3 (C-12), 22.6 (C-13), 123.5 (C-14), 132.2 (C-15), 25.6 (C-16), 17.6 (C-17), 26.7 (C-18), *assignments for C-2 and C-3 may be reversed; $^1H$ NMR ($CDCl_3$) 67 1.42 (s, 3H), 1.53 (s, 3H), 1.63 (s, 3H), 1.63 (m, 1H), 1.73 (m, 1H), 2.08 (m, 2H), 5.05 (bt, J=7.0 Hz, 1H), 5.88 (d, J=10.5 Hz, 1H), 6.80 (d, J=10.0 Hz, 1H), 6.83 (d, J=10.0 Hz, 1H), 7.05 (d, J=8.5 Hz, 1H), 7.79 (d, J=10.5 Hz, 1H), 7.92 (d, J=8.5 Hz, 1H).

Finally, 5 mg of compound 8 were mixed with 10 mg of teretifolione B (2) in 0.9 ml pyridine, and the reaction solution was heated at around 800 for 90 min. The reaction mixture was then evaporated to dryness and purified by HPLC on a phenyl column, eluting with $CH_3CN/H_2O$ (17:3, 0.05% TFA by vol). Final HPLC purification on the same column, using $CH_3CN/H_2O$ (9:1, 0.05% TFA by vol), provided 1.2 mg of material ($[\alpha]_D$=+1750°, c 0.09, MeOH), which by IR, UV, $^1H$ NMR, HPLC retention, and anti-HIV activity profile was identical to naturally occurring conocurvone (1).

The fact that both the natural and synthetic conocurvone had identical $^1H$ NMR spectra, including all of the minor satellite peaks, supported the fact that conocurvone exists as an equilibrium mixture of tautomers and atropisomers. The optical rotation of the synthetic material ($[\alpha]_D$=+175°) was essentially identical with that measured for the natural product ($[\alpha]_D$=+184°).

While the above syntheses of active compounds 1 and 4 utilized as a precursor teretifolione B (2) which could be obtained (Example 1, above) in substantially pure form from Conospermum sp., it is obvious that other plants, such as other species of Conospermum, also contain teretifolione B (2) (Cannon, J. R., et al., *Tetrahedron Lett.*, 2795–2598, 1975), which can also be used as a precursor for synthesis of compounds 1 and 4 as described above. Also, since it is known that the racemic form of compound 2 can be prepared entirely by chemical synthesis (Cannon, J. R., et al., *Tetrahedron Lett.*, 2795–2798, 1975), it is obvious that racemic compound 2 could be used to prepare racemic compound 1 by total synthesis according to the same procedure described above. Alternatively, appropriate chiral precursors could be used to synthesize pure enantiomers of compound 2, which in turn could be used to prepare the individual stereochemical isomers of compound 1. However, any or all of the stereoisomers of compound 1 or 4 would be expected to have useful antiviral activity, since there is no evidence that the chirality at the C-11 position of the teretifolione B subunits of compound 1 or 4 is essential for antiviral activity. This is further reinforced by the synthesis and antiviral activity of compounds 9 and 10, which are also "trimeric" naphthoquinone compounds but which lack any chiral centers in the subunits.

Compound 9 is a novel synthetic product which has not been previously described in the chemical literature. It was prepared as follows. Into 1 ml pyridine were added 34 mg 1,4-naphthoquinone and 70 mg 2-hydroxy-1,4-naphthoquinone. The reaction mixture was heated in a water bath at 80° for 90 min. and then the pyridine was removed under vacuum. The resulting gum was washed with 2N HOAc, solubilized in MeOH/CH$_2$Cl$_2$, and coated onto phenyl bonded-phase packing. The coated sorbent was added to the top of a 4×2 cm VLC column and eluted with increasing concentrations of CH$_3$CN in H$_2$O. Material that eluted with 6:4 CH$_3$CN/H$_2$O was pooled, based upon its TLC characteristics, to give an 8.2 mg fraction that was further purified by phenyl bonded-phase HPLC (1 cm column) with CH$_3$CN/H$_2$(6:4, 0.05% TFA by vol) to give 5.1 mg of compound 9. For compound 9: LRMS m/z 502, appropriate for C$_{30}$H$_{14}$O$_8$; $^1$H NMR (CDCl$_3$) 67 7.65–74 (m, 3H), 7.76–7.82 (m, 3H), 8.04–8.09 (m, 3H), 8.14–8.19 (m, 3H); $^{13}$C NMR (CDCl$_3$) δ 116.9, 117.3, 125.9, 126.2, 126.4, 126.6, 126.7, 129.7, 129.8, 132.1, 132.2, 132.3, 132.9, 133.0, 134.7, 141.8, 141.9, 154.6, 155.3, 180.6, 180.8, 182.0, 182.1, 182.5, 183.0.

Compound 10 is a structure previously reported in the literature (Jurd, L., *Aust. J. Chem.*, 33: 1603–1610, 1980), but which was not previously known to have antiviral activity. It was prepared for the antiviral evaluations herein by the published method (Jurd, L., *Aust. J. Chem.*, 33: 1603–1610, 1980). Briefly, into 3 ml of 50% acetic acid was added 158 mg 1,4-naphthoquinone and 162 mg 4-hydroxycoumarin. The reaction mixture was heated at 100° for 30 min. The yellow precipitate that formed was recovered by filtration, digested with 4 ml acetone and filtered again to give 107 mg of compound 10. For compound 10: LRMS m/z 478, appropriate for C$_{28}$H$_{14}$O$_8$; $^1$H NMR (DMSO-d$_6$) δ 7.27–7.31 (m, 2H), 7.32–7.37 (m, 2H), 7.60–7.65 (m, 2H), 7.87–7.91 (m, 2H), 7.93–7.96 (m, 2H), 8.10–8.14 (m, 2H).

EXAMPLE 4

This example illustrates a generic series of antiviral naphthoquinone compounds of the present invention.

One skilled in the art will appreciate that other antiviral naphthoquinone compounds, in addition to those of Example 3, may be isolated in substantially pure form from natural sources and/or synthesized chemically. Antiviral naphthoquinone compounds can comprise four distinct series (A–D), as illustrated more generally in FIGS. 4A–D, wherein R$_1$–R$_{12}$ each are the same or different, and each may be H, C$_1$–C$_{10}$ straight-chain or branched-chain, saturated or unsaturated alkyl, an aryl, OCH$_3$, or OH. For example, conocurvone (1) is of series A (FIG. 4A), wherein R$_1$=R$_6$=R$_{12}$=(CH$_2$)$_2$CHC(CH$_3$)$_2$; R$_2$=R$_5$=R$_{11}$=CH$_3$; R$_3$=R$_4$=R$_7$=R$_8$=R$_9$=R$_{10}$=H. Similarly, compound 4 of Example 3 above is of series B (FIG. 4B), wherein R$_1$=R$_2$=R$_3$=R$_4$=R$_7$=R$_8$=R$_9$=R$_{10}$=H; R$_6$=R$_{12}$=(CH$_2$)$_2$CHC(CH$_3$)$_2$; R$_5$=R$_{11}$=CH$_3$. Likewise, compound 9 of Example 3 above is of series C (FIG. 4C), wherein R$_1$–R$_{12}$ are the same, and each is H. Finally, compound 10 of Example 3 above is of series D (FIG. 4) wherein R$_1$–R$_{12}$ are the same, and each is H.

It will be further apparent from the above examples to one skilled in the art that other members of antiviral naphthoquinone series A–D may be isolated in pure form from plants, or may be readily synthesized using the general methodology of Example 3 and the appropriate precursor compounds, which can be isolated from plants, synthesized by available methods, or obtained commercially. For example, as reported in the literature (Cannon, J. R., et al., *Tetrahedron Lett.*, 2795–2798, 1975), compounds of the structures indicated below can be isolated in pure form from plants of the genus Conospermum or can be synthesized chemically:

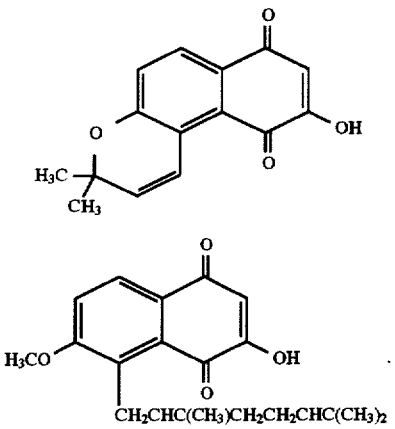

These compounds can be used as the appropriate precursors to synthesize, by the general methods of Example 3, yet further examples of antiviral naphthoquinone compounds, such as a compound of series A wherein R$_1$=R$_2$=R$_5$=R$_6$=R$_{11}$=R$_{12}$=CH$_3$; R$_3$=R$_4$=R$_7$=R$_8$=R$_9$=R$_9$R$_{10}$=H, and a compound of series B wherein R$_1$=R$_2$=R$_3$=R$_4$=R$_7$=R$_8$=R$_{10}$=H; R$_5$=R$_6$=R$_{11}$32 R$_{12}$=CH$_3$, and a compound of series C wherein R$_1$=R$_2$=R$_3$=R$_4$=R$_7$=R$_8$=R$_9$=R$_{10}$=H; R$_5$=R$_{12}$=CH$_2$CH(CH$_3$)C(CH$_2$)$_2$CHC(CH$_3$)$_2$; R$_6$=R$_{11}$=OCH$_3$. In yet another example, ismailin, a previously reported structure (Waterman, P. G., et al., *J. Chem. Res.*, (M): 101–144, 1985), not previously known to have antiviral activity, is a compound of series D wherein R$_1$=R$_3$=R$_6$=R$_7$=R$_8$=R$_9$=R$_{10}$=H; R$_2$=R$_5$=R$_{12}$=CH$_3$; R$_4$=OH.

EXAMPLE 5

This example illustrates the antiviral activity of naphthoquinone compounds of the present invention either isolated from plants of the genus Conospermum or synthesized chemically.

Pure compounds were initially evaluated for antiviral activity using an XTT-tetrazolium anti-HIV primary screening assay described previously (Boyd, M. R., *in AIDS Etiology Diagnosis, Treatment and Prevention* (DeVita, V. T., Jr., Hellman, S., Rosenberg, S. A., eds.), pp 305–319 (Philadelphia: Lippincott, 1988); Gustafson, K. R., et al., *J. Med. Chem.*, 35: 1978–1986, 1992); Weislow, O. S., et al., *J. Natl. Cancer Inst.*, 81: 577–586, 1989); Gulakowski, R. J., et al., *J. Virol. Methods*, 33: 87–100, 1991)). The CEM-SS human lymphocytic target cell line used in all assays was maintained in RPMI 1640 medium (Gibco, Grand Island, N.Y.), without phenol red, and was supplemented with 5% fetal bovine serum, 2 mM L-glutamine, and 50 μg/ml gentamicin (complete medium).

Exponentially-growing cells were pelleted and resuspended at a concentration of $2.0 \times 10^5$ cells/ml in complete medium. The Haitian variant of HIV, HTLV-III$_{RF}$ ($3.54 \times 10^6$ SFU/ml), was used throughout. Frozen virus stock solutions were thawed immediately before use and resuspended in complete medium to yield $1.2 \times 12^5$ SFU/ml. The appropriate amounts of the pure compounds for anti-HIV evaluations were dissolved in 100% dimethylsulfoxide (DMSO), then diluted in complete medium to the desired initial concentration (and with the final DMSO content not exceeding 1%). All serial drug dilutions, reagent additions, and plate-to-plate transfers were carried out with an automated Biomek 1000 Workstation (Beckman Instruments, Palo Alto, Calif.).

Table 1 provides examples of antiviral activity of naphthoquinone compounds of series A-D tested in the primary anti-HIV screening assay. Over a broad concentration range, conocurvone (1), which had been isolated in pure form from Conospermum sp. (Spjut 7139) (Example 1, above), provided complete protection ($EC_{50}$ 0.02 μM; $IC_{50}$ 50 μM) against the cytopathic effects of HIV-1 infection in the primary screening assay; likewise, conocurvone (1), which had been prepared synthetically (Example 3, above), showed equivalent antiviral activity ($EC_{50}$ 0.02 μM; $IC_{50}$ 50 μM). Compound 4 also provided complete inhibition of HIV-1 in this assay, giving an $EC_{50}=0.02$ μM and $IC_{50}=50$ μM. Compounds 9 and 10 also showed anti-HIV activity, giving $EC_{50}$'s of 16 μM and 23 μM, and $IC_{50}$'s of 48 μM and 418 μM, respectively. The critical requirement for the central "trimeric" core structure shared by all of the active compounds was further confirmed by the total lack of anti-HIV activity (data not shown) of the "dimeric" or "monomeric" relatives (such as compounds 2 and 5).

TABLE 1

Examples of Anti-HIV Activity of Naphthoquinone Compounds of Series A-D

| Compound (Ref. FIG. 1) | $EC_{50}$ (μM) | $IC_{50}$ (μM) | In Vitro TI |
|---|---|---|---|
| 1 | 0.02 | 50 | 2500 |
| 4 | 0.02 | 50 | 2500 |
| 9 | 16 | 48 | 3 |
| 10 | 23 | 418 | 18 |

As an example of a further demonstration of the anti-HIV activity of a pure naphthoquinone compound, a battery of inter-related assays was performed on an antiviral naphthoquinone compound, specifically conocurvone (1), in individual wells of 96-well microtiter plates, using methods described in detail elsewhere (Gulakowski, R. J., et al., *J. Virol. Methods*, 33: 87-100, 1991).

Briefly, the procedure was as follows. Uninfected CEM-SS cells were plated at a density of $1 \times 10^4$ cells in 50 μl of complete medium. Diluted HIV-1 virus was then added to appropriate wells in a volume of 50 μl to yield a multiplicity of infection of 0.6. Appropriate cell, virus, and drug controls were incorporated in each experiment. The final volume in each microtiter well was 200 μl. Quadruplicate wells were used for virus-infected cells, and duplicate wells were used for uninfected cells. Plates were incubated at 37° C. in an atmosphere containing 5% $CO_2$ for 4, 5, or 6 days.

Subsequently, aliquots of cell-free supernatant were removed from each well using the Biomek, and analyzed for reverse transcriptase activity, p24 antigen production, and synthesis of infectious virions as described (Gulakowski, R. J., et al., *J. Virol. Methods*, 33: 87-100, 1991). Cellular growth or viability then was estimated on the remaining contents of each well, using the XTT (Weislow, O. S., et al., *J. Natl. Cancer Inst.*, 81: 577-586, 1989), BCECF (Rink, T. L., et al., *J. Cell. Biol.*, 95: 189-196, 1982), and DAPI (McCaffrey, T. A., et al., *In Vitro Cell Develop. Biol.*, 24: 247-252, 1988) assays as described (Gulakowski, R. J., et al., *J. Virol. Methods*, 33: 87-100, 1991). To facilitate graphical displays and comparisons of data, the individual experimental assay results (of at least quadruplicate determinations of each) were averaged, and the mean values were used to calculate percentages in reference to the appropriate controls. Standard errors of the mean values used in these calculations typically averaged less than 10% of the respective mean values.

As illustrated in FIGS. 5A-D, conocurvone (1) was capable of complete inhibition of the cytopathic effects of HIV-1 upon CEM-SS human lymphoblastoid target cells in vitro; direct cytotoxicity of the compound upon the target cells was apparent only at much greater concentrations (in vitro "therapeutic index" 2500). Conocurvone also strikingly inhibited the production of RT, p24, and SFU in HIV-1-infected CEM-SS within these same inhibitory effective concentrations, indicating that the compound essentially halted viral replication.

While this invention has been described with emphasis upon preferred embodiments, it will be obvious to those of ordinary skill in the art that the preferred compounds, compositions, and methods may be varied. It is intended that the invention may be practiced otherwise than as specifically described herein. Accordingly, this invention includes all modifications encompassed within the spirit and scope of the following claims. All publications referenced herein are hereby incorporated by reference in their entireties.

What is claimed is:

1. An antiviral naphthoquinone selected from the group consisting of:

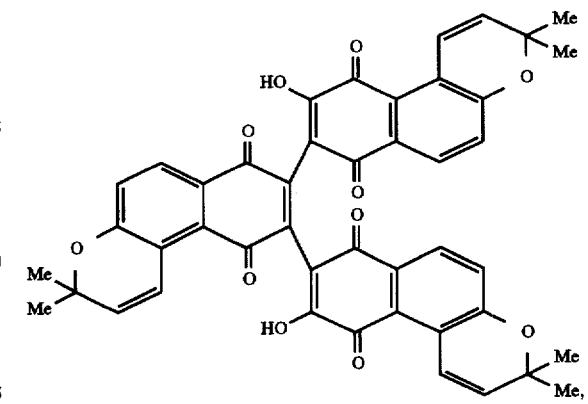

-continued

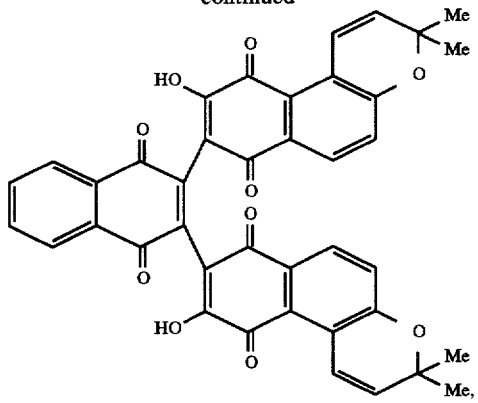

and a prodrug thereof, wherein said prodrug is an ester of the quinol formed by the reduction of said antiviral naphthoquinone.

2. The antiviral naphthoquinone of claim 1, wherein said antiviral naphthoquinone is selected from the group consisting of:

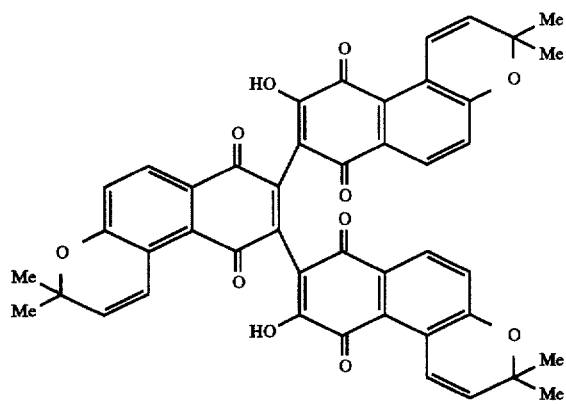

and a prodrug thereof, wherein said prodrug is an ester of the quinol formed by the reduction of said antiviral naphthoquinone.

3. The antiviral naphthoquinone of claim 1, wherein said antiviral naphthoquinone is selected from the group consisting of:

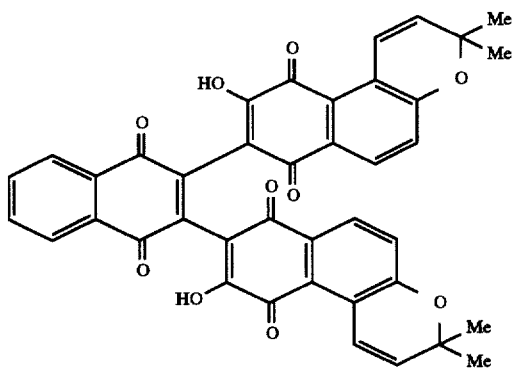

and a prodrug thereof, wherein said prodrug is an ester of the quinol formed by the reduction of said antiviral naphthoquinone.

4. The antiviral naphthoquinone of claim 2, wherein said antiviral naphthoquinone is

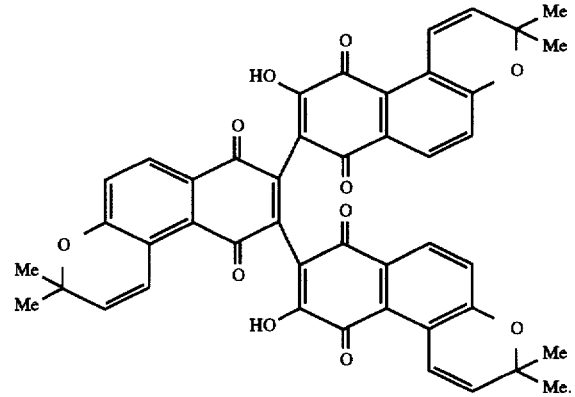

5. The antiviral naphthoquinone of claim 3, wherein said antiviral naphthoquinone is

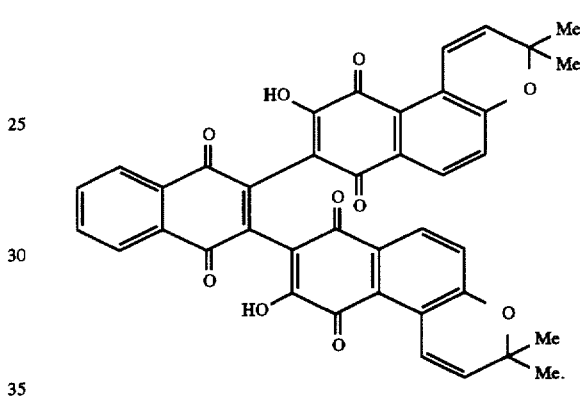

6. An antiviral composition which comprises an antiviral effective amount of at least one compound of claim 1 and a pharmaceutically acceptable carrier.

7. An antiviral composition which comprises an antiviral effective amount of the compound of claim 4 and a pharmaceutical acceptable carrier.

8. An antiviral composition which comprises an antiviral effective amount of the compound of claim 5 and a pharmaceutically acceptable carrier.

9. A method of treating a retroviral infection, which method comprises administering to a host an effective amount of at least one compound of claim 1.

10. The method of claim 9, wherein said host is human.

11. The method of claim 10, wherein said retrovirus is a human immunodeficiency virus.

12. A method of treating a retroviral infection, which comprises administering to a host an effective amount of the compound of claim 4.

13. The method of claim 12, wherein said host is a human.

14. The method of claim 13, wherein said retrovirus is a human immunodeficiency virus.

15. A method of treating a retroviral infection, which comprises administering to a host an effective amount of the compound of claim 5.

16. The method of claim 15, wherein said host is a human.

17. The method of claim 16, wherein said retrovirus is a human immunodeficiency virus.

18. A method of treating a retroviral infection, which comprises administering to a host an effective amount of at least one compound selected from the group consisting of an antiviral naphthoquinone, in substantially pure form, selected from the group consisting of:

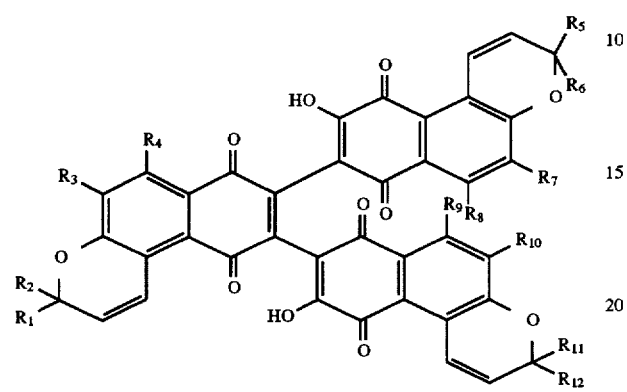

SERIES A and

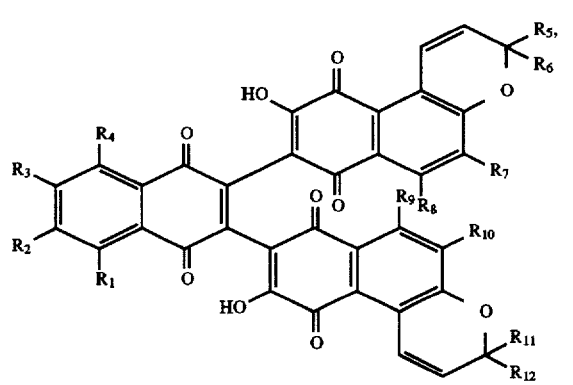

SERIES B wherein each of $R_1$–$R_{12}$ is the same or different, and each is H, a $C_1$–$C_{10}$ straight-chain or branched-chain saturated or unsaturated alkyl, an aryl, $OCH_3$, or OH.

19. The method of claim 18, wherein said compound is selected from the group consisting of the antiviral naphthoquinone of claim 1 selected from the group consisting of:

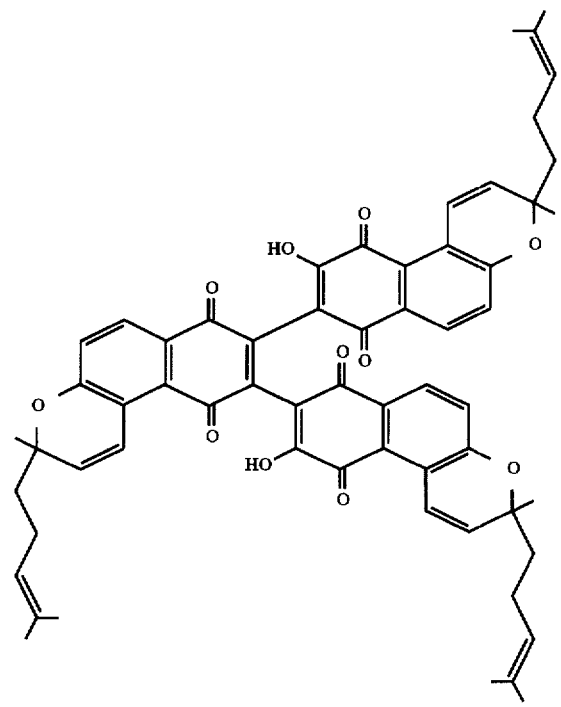

COMPOUND 1
(conocurvone)

and

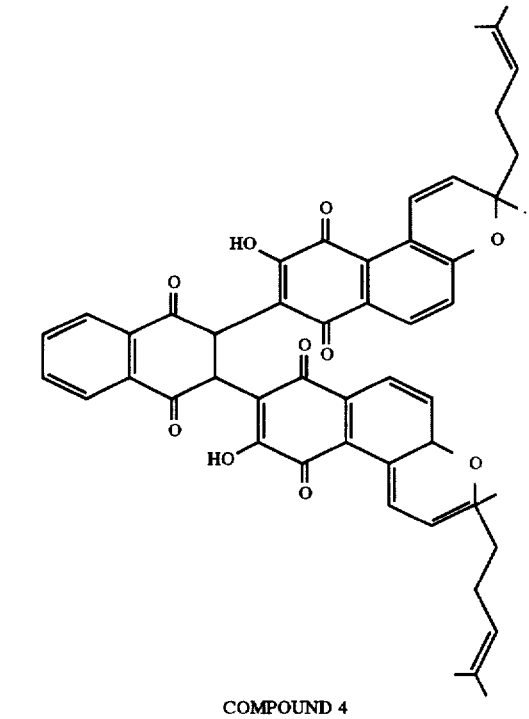

COMPOUND 4

20. The method of claim 19, wherein said host is human.
21. The method of claim 20, wherein said retrovirus is human immunodeficiency virus.

* * * * *